(12) United States Patent
Johnson et al.

(10) Patent No.: US 7,169,616 B2
(45) Date of Patent: Jan. 30, 2007

(54) METHOD OF PURGING TRAPPED GAS FROM A SYSTEM FLUID CONTAINED IN AN ACTUATION VALVE

(75) Inventors: James E. Johnson, Sebastopol, CA (US); Neil R. Picha, Petaluma, CA (US); Craig M. Storms, Cotati, CA (US); David A. Martin, Santa Rosa, CA (US)

(73) Assignee: Innovadyne Technologies, Inc., Santa Rosa, CA (US)

( * ) Notice: Subject to any disclaimer, the term of this patent is extended or adjusted under 35 U.S.C. 154(b) by 569 days.

(21) Appl. No.: 10/353,824

(22) Filed: Jan. 27, 2003

(65) Prior Publication Data

US 2003/0170903 A1    Sep. 11, 2003

Related U.S. Application Data

(60) Provisional application No. 60/351,858, filed on Jan. 25, 2002.

(51) Int. Cl.
*G01N 1/10* (2006.01)
*B01L 3/02* (2006.01)
*F16T 1/42* (2006.01)

(52) U.S. Cl. .................... 436/180; 422/100; 422/103; 137/171

(58) Field of Classification Search .............. 422/100, 422/103; 436/180; 137/171, 197; 251/129.05
See application file for complete search history.

(56) References Cited

U.S. PATENT DOCUMENTS

| | | | |
|---|---|---|---|
| 3,645,142 A | 2/1972 | Turpin | |
| 3,963,148 A | 6/1976 | Proni et al. | |
| 3,994,423 A | 11/1976 | Burg | |
| 4,013,413 A | 3/1977 | Stewart et al. | |
| 4,369,664 A | 1/1983 | Bunce et al. | |
| 4,459,267 A | 7/1984 | Bunce et al. | |
| 4,461,328 A | 7/1984 | Kenney | |
| 4,723,262 A | 2/1988 | Noda et al. | |
| 4,818,706 A | 4/1989 | Starr | |
| 4,917,351 A * | 4/1990 | Lindbloom et al. ..... | 251/129.18 |
| 5,104,621 A | 4/1992 | Pfost et al. | |
| 5,312,757 A | 5/1994 | Matsuyama et al. | |
| 5,465,582 A | 11/1995 | Bliss et al. | |
| 5,525,515 A | 6/1996 | Blattner | |
| 5,599,500 A | 2/1997 | Jones | |
| 5,649,687 A * | 7/1997 | Rosas et al. ........... | 251/129.15 |
| 5,738,728 A | 4/1998 | Tisone | |
| 5,741,554 A | 4/1998 | Tisone | |
| 5,743,960 A | 4/1998 | Tisone | |
| 5,820,824 A | 10/1998 | Tamaka | |
| 5,833,925 A | 11/1998 | Shu et al. | |
| 5,849,598 A | 12/1998 | Wilson et al. | |
| 5,916,524 A * | 6/1999 | Tisone ........................ | 422/100 |
| 5,955,373 A | 9/1999 | Hutchins et al. | |
| 5,985,214 A | 11/1999 | Stylli et al. | |
| 6,033,911 A | 3/2000 | Schultz et al. | |
| 6,040,186 A | 3/2000 | Lewis et al. | |
| 6,045,755 A | 4/2000 | Lebl et al. | |
| 6,063,339 A | 5/2000 | Tisone et al. | |
| 6,066,298 A | 5/2000 | Fukunaga | |
| 6,068,393 A | 5/2000 | Hutchins et al. | |
| 6,083,763 A | 7/2000 | Balch | |
| 6,096,276 A | 8/2000 | Laursen | |
| 6,112,605 A | 9/2000 | Papen et al. | |
| 6,158,269 A | 12/2000 | Dorenkott et al. | |
| 6,182,719 B1 | 2/2001 | Yahiro | |
| 6,299,840 B1 | 10/2001 | Watanabe et al. | |
| 6,322,752 B1 | 11/2001 | Siddiqui et al. | |
| 6,323,035 B1 | 11/2001 | Kedar et al. | |
| 6,325,114 B1 | 12/2001 | Bevirt et al. | |
| 6,372,185 B1 | 4/2002 | Shumate et al. | |
| 6,432,365 B1 | 8/2002 | Levin et al. | |
| 6,503,454 B1 | 1/2003 | Hadimioglu et al. | |
| 6,537,505 B1 * | 3/2003 | LaBudde et al. ........... | 422/103 |
| 6,558,623 B1 | 5/2003 | Ganz et al. | |
| 6,605,257 B1 | 8/2003 | Nakazawa et al. | |
| 6,627,446 B1 | 9/2003 | Roach et al. | |
| 6,685,884 B2 | 2/2004 | Stylli et al. | |
| 6,730,517 B1 | 5/2004 | Koster et al. | |
| 6,846,680 B2 | 1/2005 | Friswell et al. | |
| 2001/0026772 A1 | 10/2001 | Fuerst et al. | |
| 2001/0053337 A1 | 12/2001 | Doktycz et al. | |

| | | | |
|---|---|---|---|
| 2001/0055545 | A1 | 12/2001 | Takii et al. |
| 2002/0012611 | A1 | 1/2002 | Stylli et al. |
| 2002/0012614 | A1* | 1/2002 | Koide et al. ............... 422/103 |
| 2002/0051737 | A1 | 5/2002 | Sollbohmer et al. |
| 2002/0176801 | A1 | 11/2002 | Gieberer et al. |
| 2002/0192113 | A1 | 12/2002 | Uffenheimer et al. |
| 2003/0017085 | A1 | 1/2003 | Kercso et al. |
| 2003/0021734 | A1 | 1/2003 | Van et al. |
| 2003/0022380 | A1 | 1/2003 | Jakubowicz et al. |
| 2003/0027345 | A1 | 2/2003 | Friswell et al. |
| 2004/0014228 | A1 | 1/2004 | Brignac et al. |
| 2004/0047765 | A1 | 3/2004 | Gordon et al. |
| 2005/0244303 | A1* | 11/2005 | Ingenhoven et al. ........ 422/100 |

FOREIGN PATENT DOCUMENTS

| | | |
|---|---|---|
| AU | A-32209/84 | 3/1985 |
| CA | 2 202 649 | 12/2000 |
| EP | 0 024 230 | 2/1981 |
| EP | 0 810 438 | 3/1997 |
| EP | 1197693 A2 | 4/2002 |
| EP | 1 334 770 | 1/2003 |
| FR | 1.428.878 | 2/1966 |
| WO | WO 97/26539 | 7/1997 |
| WO | WO 99/21031 | 4/1999 |
| WO | WO 99/42752 | 8/1999 |
| WO | WO 00/51736 | 9/2000 |
| WO | WO 01/04909 | 1/2001 |
| WO | WO 01/28701 | 4/2001 |
| WO | WO 01/65214 | 9/2001 |
| WO | WO 01/65214 A2 | 9/2001 |
| WO | WO 01/65214 A3 | 9/2001 |

OTHER PUBLICATIONS

Patent Abstracts of Japan, Publication No. 63-295267, Recovering Method For Ink Jet Recorder, Tokunaga Tatsuyuki, et al., published Dec. 1, 1988, filed May 27, 1987.

European Search Report dated May 9, 2005 from related application No. 03704032.6.

Ilene Schneider, Instrumentation—Doing More With Less—Discover the turnkey systems now streamlining the entire liquid handling process, *Genomics & Proteomics*, Sep. 2002.

Hue P. Le, Progress and Trends in Ink-Jet Printing Technology, *Journal Of Imaging Science And Technology*, vol. 42, No. 1, Jan./Feb. 1998, pp. 49-62.

James E. Johnson, Neil R. Picha and Mitchel J. Doktycz, *Hybrid Valve Apparatus and Method for Fluid Handling*, U.S. Appl. No. 09/689,548, filed Oct. 11, 2000.

James E. Johnson, Neil R. Picha, David A. Martin and Joel McComb, *Universal Non-Contact Dispense Peripheral Apparatus and Method For A Primary Liquid Handling Device*, U.S. Appl. No. 10/237,916, filed on Sep. 6, 2002.

Patent Abstracts of Japan, Publication No. 63295267, *Recovering Method For Ink Jet Recorder*, Moriyajma Jiro, filed May 27, 1987.

Communication under Rule1 112 EPC, European Patent Office, Nov. 10, 2004.

* cited by examiner

Primary Examiner—Brian R. Gordon
(74) Attorney, Agent, or Firm—Beyer Weaver & Thomas LLP

(57) ABSTRACT

An apparatus and method for delivering repetitive, precision, low volume liquid dispensing from a dispensing orifice of a non-contact liquid dispensing apparatus. An elongated communication passageway of the dispensing apparatus is defined by interior walls having one end in fluid communication with a system fluid reservoir and an opposite end terminating at the dispensing orifice. A system fluid is placed in the communication passageway extending substantially continuously from the system fluid reservoir to the dispensing orifice. A relatively small volume of gaseous fluid is aspirated through the dispensing orifice, and into the communication passageway in a manner such that the gaseous fluid extends substantially continuously across the transverse cross-sectional dimension of the communication passageway. Subsequently, a dispensing liquid is aspirated through the dispensing orifice and into the communication passageway in a manner such that the relatively small volume of aspirated gaseous fluid forms a minute, unitary air gap fully enclosed between the interior walls of the communication passageway and a liquid interface between the system fluid and the dispensing liquid contained in the communication passageway. This minute air gap substantially prevents dispersion and dilution therebetween at the liquid interface. To effect dispensing, a rapid pressure pulse with a predetermined pulse width is applied to the system fluid upstream from the minute air gap, causing the pressure pulse to traverse the minute air gap to the dispensing liquid without substantial fluid compression of the minute air gap. This enables substantially accurate, relatively small volume, non-contact liquid dispensing of the dispensing liquid from the dispensing orifice.

42 Claims, 18 Drawing Sheets

| Count | Pulse Width (ms) | Calc Freq (Hz) | Actual Freq (Hz) |
|---|---|---|---|
| nBuzzCount = 20; | nBuzzDwell = 100; | 10 | 8 |
| nBuzzCount = 23; | nBuzzDwell = 80; | 13 | 10 |
| nBuzzCount = 30; | nBuzzDwell = 65; | 15 | 13 |
| nBuzzCount = 40; | nBuzzDwell = 50; | 20 | 17 |
| nBuzzCount = 50; | nBuzzDwell = 40; | 25 | 21 |
| nBuzzCount = 66; | nBuzzDwell = 30; | 33 | 28 |
| nBuzzCount = 100; | nBuzzDwell = 20; | 50 | 42 |
| nBuzzCount = 133; | nBuzzDwell = 15; | 67 | 56 |
| nBuzzCount = 160; | nBuzzDwell = 12; | 83 | 70 |
| nBuzzCount = 200; | nBuzzDwell = 10; | 100 | 84 |
| nBuzzCount = 290; | nBuzzDwell = 7; | 143 | 120 |
| nBuzzCount = 400; | nBuzzDwell = 5; | 200 | 168 |
| nBuzzCount = 500; | nBuzzDwell = 4; | 250 | 210 |
| nBuzzCount = 670; | nBuzzDwell = 3; | 333 | 280 |
| nBuzzCount = 1000; | nBuzzDwell = 2; | 500 | 420 |

*FIG. 7*

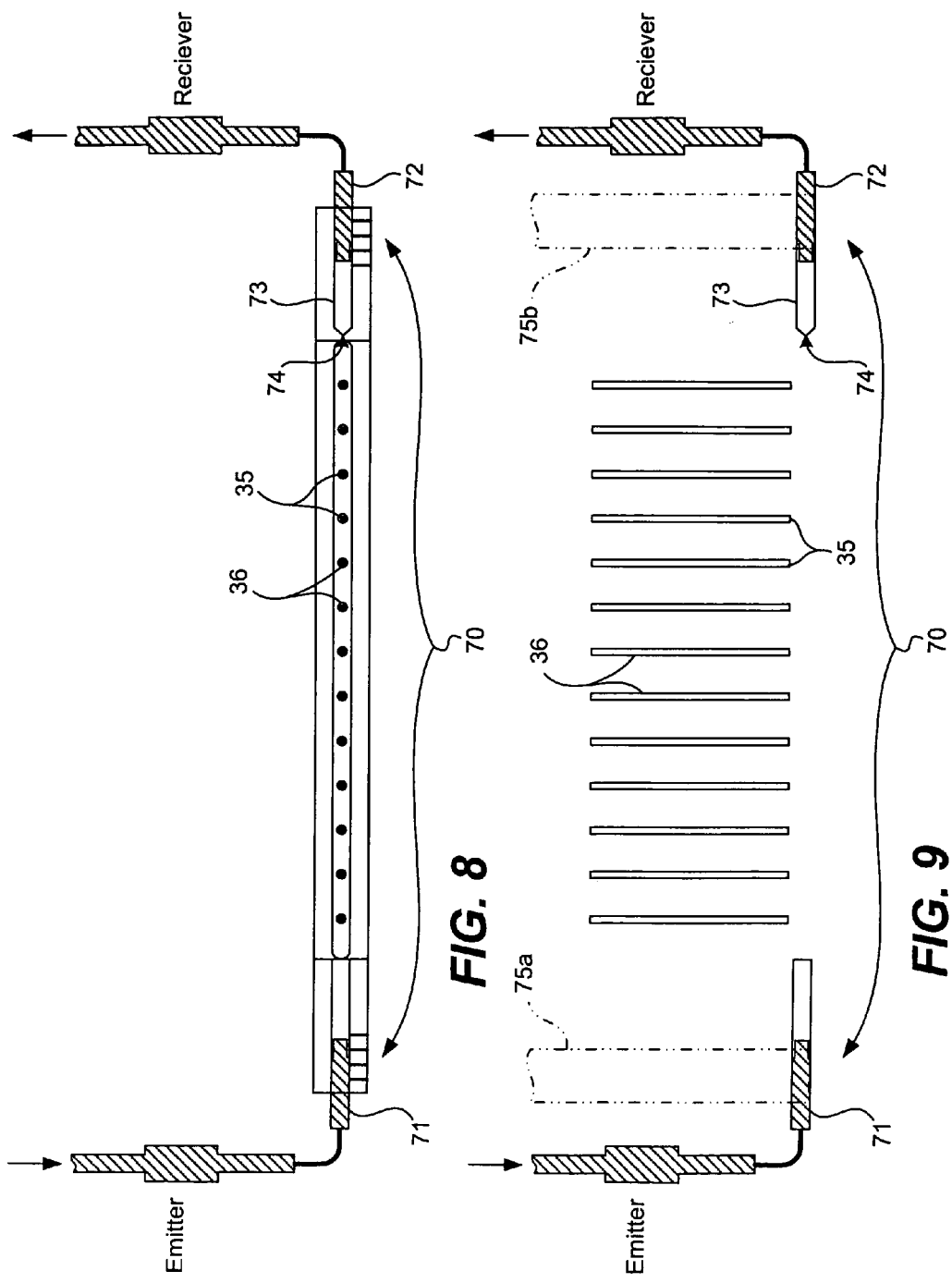

Instrument        Apps Inst 007
Density (g/mL)    0.9977735
Temperature       23°C Gravimetric Calibration Curve

TABLE II

| Sequence | Pulse Width(us) | Volume Per tip (uL) |
|---|---|---|
| 1 | 3600 | 0.097 |
| 2 | 4560 | 0.121 |
| 3 | 5760 | 0.147 |
| 4 | 7300 | 0.184 |
| 5 | 9240 | 0.253 |
| 6 | 11700 | 0.341 |
| 7 | 14800 | 0.443 |
| 8 | 18720 | 0.601 |
| 9 | 23700 | 0.833 |
| 10 | 30000 | 1.169 |

FIG._11

| Gravimetric Calibration Curve | | | Instrument | Apps Inst 007 | | | | | |
|---|---|---|---|---|---|---|---|---|---|
| | | | Density (g/mL) | 0.9977735 | Temperature(C) | 23 | | | |
| Sequence | Pulse Width(us) | Replicates | Tare(g) | Total(g) | Mass Dispensed(g) | Volume Total | Volume Per Tip(mL) | Volume Per Tip(µL) | Volume Per Tip(nL) |
| 1 | 3600 | 200 | 2.27023 | 2.42480 | 0.15457 | 0.154915 | 0.000097 | 0.097 | 96.8 |
| 2 | 4560 | 158 | 2.27917 | 2.43130 | 0.15213 | 0.152469 | 0.000121 | 0.121 | 120.6 |
| 3 | 5760 | 125 | 2.27754 | 2.42393 | 0.14639 | 0.146717 | 0.000147 | 0.147 | 146.7 |
| 4 | 7300 | 99 | 2.28908 | 2.43465 | 0.14557 | 0.145895 | 0.000184 | 0.184 | 184.2 |
| 5 | 9240 | 78 | 2.28832 | 2.44575 | 0.15743 | 0.157781 | 0.000253 | 0.253 | 252.9 |
| 6 | 11700 | 62 | 2.28795 | 2.45655 | 0.16860 | 0.168976 | 0.000341 | 0.341 | 340.7 |
| 7 | 14800 | 49 | 2.28722 | 2.46052 | 0.17330 | 0.173687 | 0.000443 | 0.443 | 443.1 |
| 8 | 18720 | 38 | 2.27674 | 2.45890 | 0.18216 | 0.182566 | 0.000601 | 0.601 | 600.5 |
| 9 | 23700 | 30 | 2.27956 | 2.47898 | 0.19942 | 0.199865 | 0.000833 | 0.833 | 832.8 |
| 10 | 30000 | 24 | 2.28659 | 2.51050 | 0.22391 | 0.22441 | 0.001169 | 1.169 | 1168.8 |
| 11 | 23700 | 30 | 2.27007 | 2.47141 | 0.20134 | 0.201789 | 0.000841 | 0.841 | 840.8 |
| 12 | 30040 | 24 | 2.27898 | 2.50504 | 0.22606 | 0.226564 | 0.001180 | 1.180 | 1180.0 |
| 13 | 38080 | 19 | 2.27733 | 2.52553 | 0.24820 | 0.248754 | 0.001637 | 1.637 | 1636.5 |
| 14 | 48260 | 15 | 2.28893 | 2.55772 | 0.26879 | 0.26939 | 0.002245 | 2.245 | 2244.9 |
| 15 | 61160 | 12 | 2.28819 | 2.57938 | 0.29119 | 0.29184 | 0.003040 | 3.040 | 3040.0 |
| 16 | 77500 | 10 | 2.28778 | 2.61118 | 0.32340 | 0.324122 | 0.004052 | 4.052 | 4051.5 |
| 17 | 98240 | 10 | 2.28700 | 2.71452 | 0.42752 | 0.428474 | 0.005356 | 5.356 | 5355.9 |
| 18 | 124500 | 10 | 2.27659 | 2.83632 | 0.55973 | 0.560979 | 0.007012 | 7.012 | 7012.2 |
| 19 | 157800 | 10 | 2.27937 | 3.00821 | 0.72884 | 0.730466 | 0.009131 | 9.131 | 9130.8 |
| 20 | 200000 | 10 | 2.28636 | 3.22602 | 0.93966 | 0.941757 | 0.011772 | 11.772 | 11772.0 |
| 21 | 157800 | 10 | 2.27025 | 3.00265 | 0.73240 | 0.734034 | 0.009175 | 9.175 | 9175.4 |
| 22 | 186200 | 10 | 2.27918 | 3.1523 | 0.87312 | 0.875068 | 0.010938 | 10.938 | 10938.4 |
| 23 | 219720 | 10 | 2.27745 | 3.31975 | 1.04230 | 1.044626 | 0.013058 | 13.058 | 13057.8 |
| 24 | 259280 | 10 | 2.28897 | 3.52969 | 1.24072 | 1.243489 | 0.015544 | 15.544 | 15543.6 |
| 25 | 305960 | 10 | 2.28830 | 2.76225 | 1.47395 | 1.477239 | 0.018465 | 18.465 | 18465.5 |
| 26 | 361040 | 8 | 2.28786 | 3.68887 | 1.40101 | 1.404136 | 0.021940 | 21.940 | 21939.6 |
| 27 | 426020 | 8 | 2.28648 | 3.95018 | 1.66370 | 1.667412 | 0.026043 | 26.053 | 26053.3 |
| 28 | 502720 | 8 | 2.28711 | 4.26044 | 1.97333 | 1.977733 | 0.030902 | 30.902 | 30902.1 |
| 29 | 593220 | 8 | 2.27673 | 4.60912 | 2.33239 | 2.337595 | 0.036525 | 36.525 | 36524.9 |
| 30 | 700000 | 8 | 2.27952 | 5.03842 | 2.75890 | 2.765056 | 0.043204 | 43.204 | 43204.0 |

*FIG. 13*

TABLE IV

| Base Reps | | 200 | | | | |
|---|---|---|---|---|---|---|
| Xtal | | 20 | Base Pulse | 720000 | | |
| | | Calculated | Pulse | Periods | Calibration | Replicate |
| Volume | 0.1 – 1.0μL | Pulse (us) | Range | Pulse (us) | Pulse (us) | Pulses |
| Low Pulse | 3600 | 3600 | | 180 | 3600 | 200 |
| High Pulse | 30000 | 4556 | 956 | 228 | 4560 | 158 |
| Range | 8.333333 | 5766 | 1210 | 288 | 5760 | 125 |
| Multiplier | 1.265649 | 7298 | 1532 | 365 | 7300 | 99 |
| | | 9237 | 1939 | 462 | 9240 | 78 |
| | | 11691 | 2454 | 585 | 11700 | 62 |
| | | 14797 | 3106 | 740 | 14800 | 49 |
| | | 18728 | 3931 | 936 | 18720 | 38 |
| | | 23703 | 4975 | 1185 | 23700 | 30 |
| | | 30000 | 6297 | 1500 | 30000 | 24 |

| Base Reps | | 30 | Base Pulse | 711000 | | |
|---|---|---|---|---|---|---|
| | | Calculated | Pulse | Periods | Calibration | Replicate |
| Volume | 1.0 – 10.0μL | Pulse (us) | Range | Pulse (us) | Pulse (us) | Pulses |
| Low Pulse | 23700 | 23700 | | 1185 | 23700 | 30 |
| High Pulse | 200000 | 30038 | 6338 | 1502 | 30040 | 24 |
| Range | 8.438819 | 38071 | 8033 | 1904 | 38080 | 19 |
| Multiplier | 1.267419 | 48252 | 10181 | 2413 | 48260 | 15 |
| | | 61155 | 12903 | 3058 | 61160 | 12 |
| | | 77509 | 16354 | 3875 | 77500 | 9 |
| | | 98236 | 20727 | 4912 | 98240 | 7 |
| | | 124506 | 26270 | 6225 | 124500 | 6 |
| | | 157801 | 33295 | 7890 | 157800 | 5 |
| | | 200000 | 42199 | 10000 | 200000 | 4 |

| Base Reps | | 5 | Base Pulse | 789000 | | |
|---|---|---|---|---|---|---|
| | | Calculated | Pulse | Periods | Calibration | Replicate |
| Volume | 10.0 – 40.0μL | Pulse (us) | Range | Pulse (us) | Pulse (us) | Pulses |
| Low Pulse | 157800 | 157800 | | 7890 | 157800 | 5 |
| High Pulse | 700000 | 186207 | 28407 | 9310 | 186200 | 4 |
| Range | 4.435995 | 219727 | 33520 | 10986 | 219720 | 4 |
| Multiplier | 1.180016 | 259281 | 39554 | 12964 | 259280 | 3 |
| | | 305956 | 46675 | 15298 | 305960 | 3 |
| | | 361033 | 55077 | 18052 | 361040 | 2 |
| | | 426025 | 64992 | 21301 | 426020 | 2 |
| | | 502716 | 76691 | 25136 | 502720 | 2 |
| | | 593213 | 90497 | 29661 | 593220 | 1 |
| | | 700001 | 106788 | 35000 | 700000 | 1 |

FIG. 19

METHOD OF PURGING TRAPPED GAS FROM A SYSTEM FLUID CONTAINED IN AN ACTUATION VALVE

RELATED APPLICATION DATA

The present application claims priority under 35 U.S.C. §119 to U.S. Provisional Application Ser. No. 60/351,858, naming Johnson et al. inventors, and filed Jan. 25, 2002, and entitled METHODS FOR HIGH-PERFORMANCE, LOW-VOLUME DISPENSING, the entirety of which is incorporated herein by reference in its entirety for all purposes.

TECHNICAL FIELD

The present invention relates to methods and apparatus for liquid handling, and more particularly, relates to methods and apparatus for non-contact, high performance, relatively low volume liquid dispensing.

BACKGROUND ART

Advances in Life Sciences, particularly in genomics and proteomics, have greatly increased the potential number of reactions and analyses that must be performed by the biotechnology and pharmaceutical industries. An estimated 30 million tests are required to screen a typical pharmaceutical company's compound library against target receptors. The typical number of tests will increase dramatically as information is gleaned from the sequencing of the human genome. To meet these increasing throughput demands in an economically feasible manner, miniaturization of tests is imperative.

Technological advances are enabling the demonstration and use of microscale chemical/biochemical reactions for performing various types of analyses. Implementation of these reactions at such smaller scales offer economies that are unmatched by conventional approaches. Reduced volumes can lower costs by an order of magnitude but conventional liquid-handling devices fail at the required volumes. Parallel implementation provides even greater advantages as demonstrated by the use of high-density plates for screening and high-density MALDI-TOF plates for mass spectrometry analyses of proteins. The rate-limiting hardware is low volume liquid transfer technology that is robust and scalable for compounds of interest. With growing demand, the development of fluid handling devices adept at manipulating sub-microliter volumes of multiple reagents is needed.

Current systems for handling liquid reagents often employ a "pick and place" technique where a liquid reagent sample from a source plate, usually a microtiter plate, is picked up and placed into another reservoir known as the target plate. This technique is often applied for replicating plates, where scale reduction between the source and the target plates are beneficially realized. Typically, an appropriate volume is aspirated from a source plate and deposited to a target site on a multiple target plate. In this arrangement, reduced sample volumes and sample spacing are required for higher degrees of miniaturization. These liquid handling systems can broadly be categorized into two liquid dispensing types: contact liquid dispensing devices and non-contact liquid dispensing devices.

One such type of contact liquid handling is capillary contact dispensing where physical contact is necessary for fluid transfer of liquid reagents. By way of example, applying a thin, elongated pin tool, the tip of which is dipped into a liquid reagent sample in the source plate, and then maneuvered into physical contact with a substrate surface at the target site of the target plate for deposit of the liquid reagent sample thereon. Through capillary action, a certain amount of liquid will adhere to the tip, and can then be transferred to the target site upon contact.

This approach, however, is inherently volumetrically inaccurate since the amount of fluid adhered to the pin tool surface can vary with each cycle. Moreover, due to "wicking" of the drops, relatively small dispensing volumes, on the order of picoliters, cannot be repetitively attained with the sufficient accuracy required for scaled-down, high throughput screening assays when delivering on dry surfaces. Further, to estimate the delivery volume, several physical properties and parameters must be considered. These include the surface tension of the liquid reagent, the hydraulic state of the substrate surface, the affinity for the substrate surface of the reagent fluid, the affinity for the pin tool surface of the reagent fluid, the momentum of the delivery contact, and the application of biochemical coatings on the substrate surface just to name a few. Another problem associated with this capillary contact dispensing technique is that it is more vulnerable to inadvertent cross-contamination of the tool tip and target sites, especially when manipulating multiple reagents and the target site density is high. Further, fragile biochemical coatings are often employed on the surface of the test sites that can be easily damaged by the tips of the pin tools during depository contact therebetween.

Regarding non-contact type liquid dispensing systems, liquid dispensing is performed without any physical contact between the dispensing device and the targeted substrate surface. Typically these systems include positive displacement, syringe-based liquid handlers, piezoelectric dispensers and solenoid-based dispensers, each technology of which affords their own advantages and disadvantages. Piezoelectric-based systems, for example, are capable of accurate delivery of low volume liquid handling tasks on the order of picoliters. Further, these devices are used with positional-accurate motion control platforms that enable increased test site array density.

While this approach is capable of accurate reagent delivery of low volumes on the order of picoliters, one problem associated with these systems is that dedicated or fixed sample reservoirs are required which are directly fluidly coupled to the dispense orifices of the piezoelectric head. The application of this non-contact technique, however, is labor intensive when sub-microliter volumes of multiple reagents are required. Moreover, volumetric precision, at picoliter levels are in part due to small dispensing orifice diameters that are subject to frequent plugging. The scalability of these systems is also reduced since the small diameter of the orifice significantly limits the volume dispense per pulse.

Solenoid-based actuation for non-contact liquid dispensing, on the other hand, tend to be significantly more versatile and scalable compared to the piezoelectric-based liquid dispenser systems. Using conventional aspiration techniques to draw liquid reagent sample into a flow path or communication passageway (e.g., of a tube) of the system, relatively larger volumes or replicate smaller volumes can be dispensed with high precision by the solenoid.

One problem associated with these designs, however, is that the solenoid base actuator must be positioned in-line with the dispense flow path. Accordingly, the flow of drawn reagent sample through the components of the dispensing actuator can cause detrimental stiction. Ultimately, volumetric delivery imprecision results, as well a prematurely reducing the life of the dispensing actuator.

To address this problem, other compatible system fluids (typically filtered de-ionized water) are applied upstream from the aspirated liquid reagents to eliminate contact of the reagent with the dispensing actuator. This bi-fluid delivery approach has proven successful for dispensing a wide range of repetitive dispensing volumes. However, the aspiration of large overfill volumes is required due to dispersion or dilution effect at the liquid interface between the sample/reagent and the system fluid. This especially holds true with repetitive liquid dispensing where the repetitive actuation of the solenoids causes increased agitation at the fluid interface. As shown in the chart of FIG. 1 (illustrating the measured concentration of the dispensed reagent sample versus the dispense sequence), the measured concentration of the liquid reagent sample significantly degrades after around the $50^{th}$ to the $60^{th}$ discharge, although the volumetric accuracy remains constant.

Accordingly, a scaleable, non-contact, liquid handling system and method is desired that provides repetitive, low volume, non-contact liquid dispensing without the degradation in liquid sample/reagent concentration, and with volumetric precision ranging from microliters to nanoliters to.

DISCLOSURE OF INVENTION

The present invention provides an apparatus and method for delivering repetitive, precision, low volume liquid dispensing from a dispensing orifice of a non-contact liquid dispensing apparatus. An elongated communication passageway of the dispensing apparatus is defined by interior walls having one end in fluid communication with a system fluid reservoir and an opposite end terminating at the dispensing orifice. A system fluid is placed in the communication passageway extending substantially continuously from the system fluid reservoir to the dispensing orifice. A relatively small volume of gaseous fluid is aspirated through the dispensing orifice, and into the communication passageway in a manner such that the gaseous fluid extends substantially continuously across the transverse cross-sectional dimension of the communication passageway. Subsequently, a dispensing liquid is aspirated through the dispensing orifice and into the communication passageway in a manner such that the relatively small volume of aspirated gaseous fluid forms a minute, unitary air gap fully enclosed between the interior walls of the communication passageway and a liquid interface between the system fluid and the dispensing liquid contained in the communication passageway. This air gap substantially prevents dispersion and dilution therebetween at the liquid interface. To effect dispensing, a rapid pressure pulse with a predetermined pulse width is applied to the system fluid upstream from the minute air gap, causing the pressure pulse to traverse the minute air gap to the dispensing liquid without substantial fluid compression of the minute air gap. This enables substantially accurate, relatively small volume, non-contact liquid dispensing of the dispensing liquid from the dispensing orifice.

Accordingly, it has been found that aspirating smaller volumes of in-line gas significantly improve the volumetric dispensing precision and reproducibility not capable with volumes greater than about 5.0 microliters. Applying a single, continuous air gap in the range of about 250 nanoliters to about 2.0 microliters, extending across the transverse cross sectional dimension of the communication passageway, precision low volume, non-contact, liquid dispensing can be delivered from these non-contact, liquid dispensing devices while maintaining sufficient separation of the liquids at the interface to minimize dispersion and dilution by the system fluid.

These discrete air gaps essentially behave as substantially incompressible fluids, unlike air gaps larger than about 10 microliters for the given diameters. As the pressure pulse propagates down the communication passageway (originating from the back pressure and the opening and closing of the dispensing actuator as will be described below), the pressure pulse can traverse this discrete air gap interface without significant loss of energy due to compliance. This enables greater control of the pressure pulse across the dispensing orifice for repetitive, precise, low volume, non-contact liquid dispensing in the picoliter to microliter. In one specific embodiment, the system fluid is pressurized with a gas at a substantially constant back pressure. Thus, a rapid actuation dispensing valve in fluid communication with the communication passageway, positioned downstream from the system fluid reservoir and upstream from the air gap, can be actuated to perform fluid flow. The back pressure, in one arrangement, is in the range of about 2.0 psi to about 15.0 psi, and preferably about 8.0 psi. The pressurizing gas may be selected as one that suppresses in-gassing, and is substantially insoluble to the system fluid. One such gas is helium.

The air gap is preferably metered into the dispensing orifice through a metered analytical aspiration device, fluidly coupled to the communication passageway. One such device is a metered analytical syringe. The dispensing liquid may also be metered into the communication passageway through this aspiration device, maintaining the air gap greater than about 1.0 to about 3.0 inches from the dispensing valve.

In another aspect of the present invention, trapped gases in a system fluid contained in an actuation valve may be purged and expelled through the dispensing orifice of these non-contact liquid handling systems. The system fluid is initially flowed through the actuation valve and into the communication passageway between the one end of the pressure tube and the dispensing orifice such that the actuation valve and the communication passageway are converted from a dry state to a hydraulic state. By rapidly actuating the actuation valve between a closed condition, preventing flow of the system fluid through the actuation valve from the system fluid reservoir to the dispensing orifice, and an opened condition, enabling fluid flow of the system fluid through the communication passageway, trapped gases in the actuation valve and corresponding communication passageway may be purged and expelled through the dispensing orifice.

The rapid actuation of the actuation valve at the respective discrete frequencies is preferably performed for the respective predetermined periods of time at a set number of times. Moreover, the rapid actuation of the actuation valve is preferably performed by varying the actuation frequency at a plurality of set discrete frequencies. Each actuation at one of the discrete frequencies is performed for a respective predetermined period of time, and for a respective set number of times. In one example, the plurality of discrete frequencies are in the range of about 1 Hz to about 1750 Hz, while in another example, the plurality of discrete frequencies are in the range of about 10 Hz to about 420 Hz.

The varying the actuation frequency may be performed by a ramped frequency sweep, incrementally increasing the actuation frequency at the discrete frequencies. Alternatively, the varying the actuation frequency is performed by a ramped frequency sweep, incrementally decreasing the actuation frequency at the discrete frequencies.

In multi-channel liquid handling devices, the purging technique is also applicable. The system fluid may be flowed into each respective communication passageway between the one end of each respective pressure tube and the respective dispensing orifice thereof such that each actuation valve and each the communication passageway is converted from a dry state to a hydraulic state. Subsequently, the corresponding actuation valve for each channel may be rapidly actuated between a respective closed condition and a respective opened condition. Each actuation is performed at a discrete actuation frequency for a respective predetermined period of time such that trapped gases contained in each respective actuation valve and each respective communication passageway are purged and expelled through the respective dispensing orifice.

In this multi-channel configuration, each of the actuation valves can be actuated for substantially the same time period to respectively dispense system fluid from each dispensing orifice of the respective pressure tube. The respective dispensed volume from each channel can be measured. By calculating the mean variance of the measured volumes, and comparing the actual measured volume dispensed from a particular channel to the mean variance, it can be determined whether the purge routine was successful. This is determined by whether the measured volume differed from the mean variance by more than a predetermined percentage. This predetermined percentage is in the range of about 3% to about 7%, and more preferably about 5%. Should the predetermined percentage be exceeded, the routine is repeated.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIG. 7 is a Table of one specific set of frequencies utilized in the "purge" routine in accordance with the present invention.

FIG. 8 is an enlarged, fragmentary bottom plan view, in cross-section, of an orifice plug detection assembly constructed in accordance with the present invention, and mounted to an array of nozzles.

FIG. 9 is a fragmentary side elevation view, in cross-section, of the orifice plug detection assembly of FIG. 8.

FIG. 11 is a Table of one specific set of measured calibration points selected to construct the Calibration Profile of FIG. 10.

FIG. 13 is a Table of data relating to three specific ranges of dispensing volumes, including measured calibration points selected to construct the Calibration Profiles of FIGS. 14–18.

FIG. 19 is a Table of data relating to three specific ranges of dispensing volumes, including data for selecting the intermediary measured calibration points between the lower and upper base pulse widths.

BEST MODE OF CARRYING OUT THE INVENTION

Figure 1:
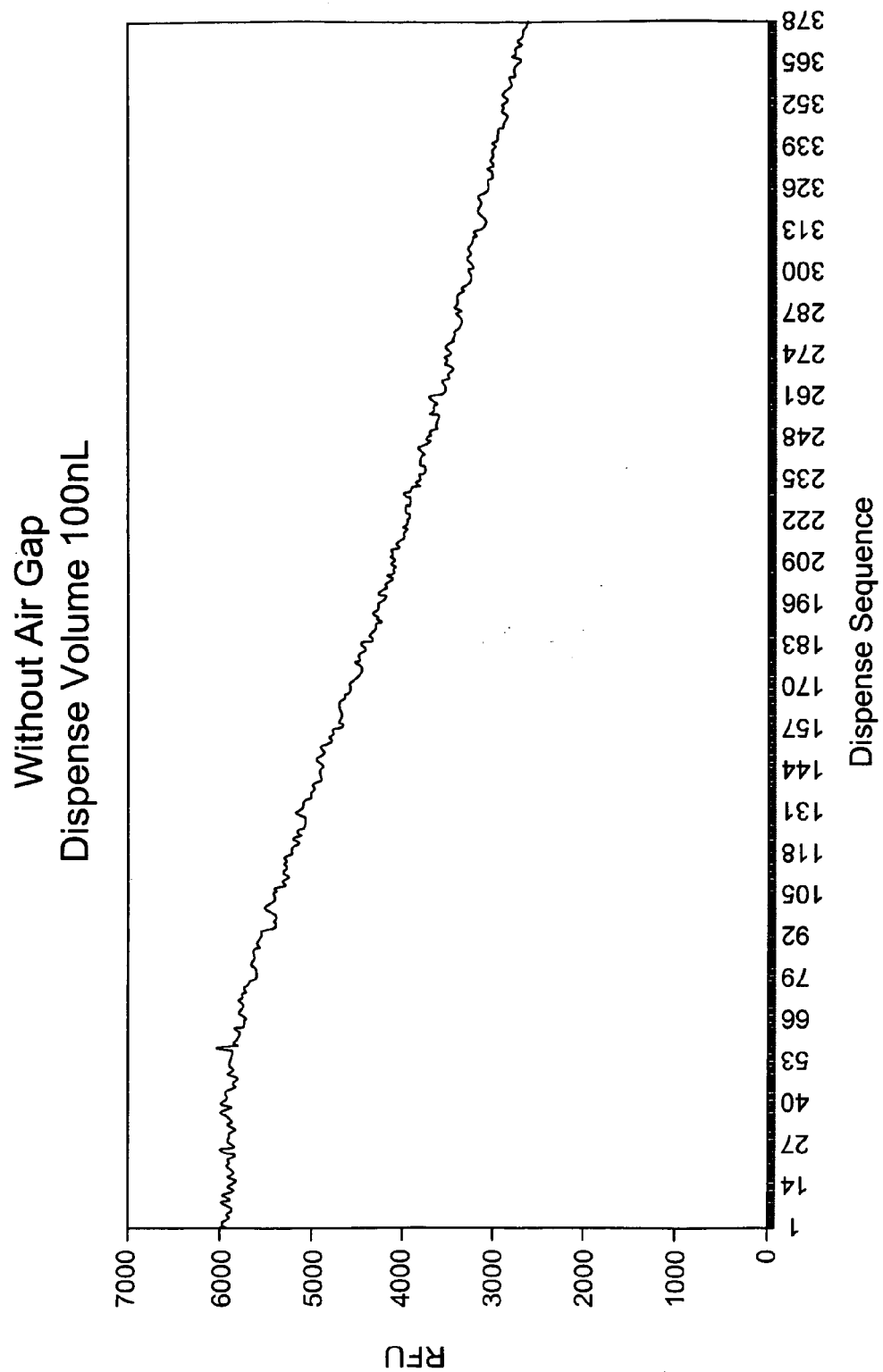
FIG. 1 is a chart illustrating the performance (measured in reagent concentration) of a sequence of 100 nl reagent dispenses utilizing a non-contact liquid dispensing system without the application of an in-line air gap.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 2:
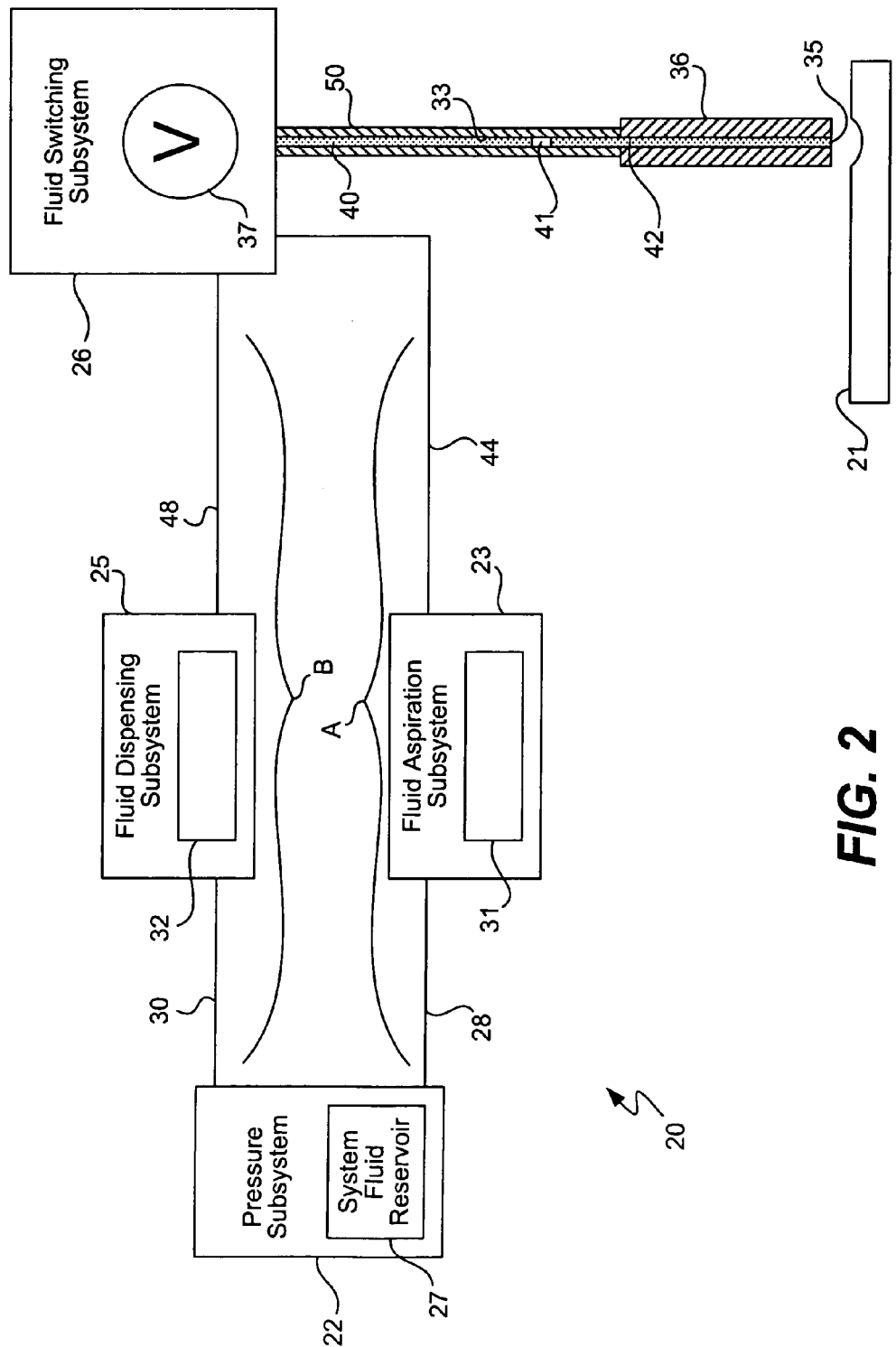
FIG. 2 is a schematic diagram of the non-contact liquid dispensing system incorporating an in-line air gap constructed in accordance with the present invention.

Referring now to FIG. 2, a non-contact liquid handling method and system, generally designated 20, is provided which is capable of precise low volume, liquid dispensing onto a target or destination substrate surface 21. Broadly, in one specific embodiment, the liquid handling system 20 includes a pressure subsystem 22, a fluid aspiration (input) subsystem 23, a fluid dispensing (output) subsystem 25 and a fluid switching subsystem 26. More particularly, the pressure subsystem 22 of the liquid handling system 20 includes a pressurized system fluid reservoir 27 independently fluidly coupled, via fluid pressure lines 28, 30, to a fluid aspiration source 31 of the fluid aspiration (input) subsystem 23, and to a fluid dispensing source 32 of the fluid dispensing (output) subsystem 25. In turn, these sources 31, 32 are independently fluidly coupled to the fluid switching subsystem 26 that provides fluid communication, via an elongated fluid communication passageway 33, to a dispensing orifice 35. In one configuration, this orifice 35 is located at the distal end of a dispensing nozzle 36 that enables both fluid aspiration and dispensing therefrom.

Figure 3:
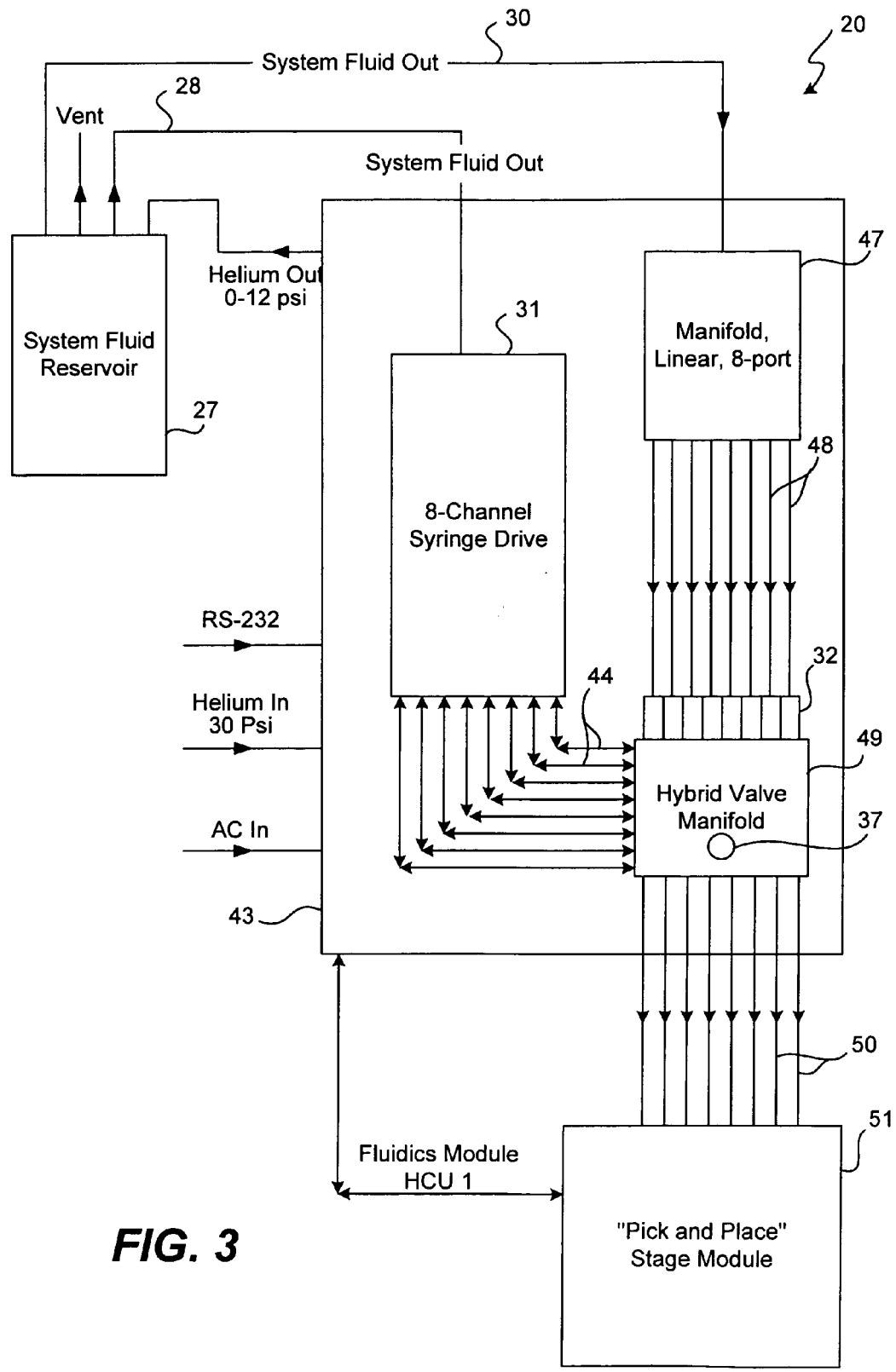
FIG. 3 is a schematic diagram of a multiple channel, non-contact, liquid dispensing system that incorporates the in-line air gap in accordance with the present invention.

Further, as best shown in FIGS. 2 and 3, the fluid flow path of the system 20 is selectably switchable, via a switching valve 37 of the switching subsystem 26, between a first fluid path A, by way of the aspiration source 31, and a second fluid path B, by way of the dispensing source 32. Thus, the first fluid path A extends from the system fluid reservoir 27 to the dispensing orifice 35, by way of the aspiration source 31, to aspirate fluids into the communication passageway, while the second fluid path B extends from the system fluid reservoir 27 to the dispensing orifice 35, by way of the dispensing source 32, to dispense fluids from the communication passageway. Essentially, the first fluid path A controls metering of the fluid input into the dispensing orifice, while the second fluid path B controls metering of the fluid from the dispensing orifice.

Similar to other solenoid-based, non-contact, liquid handling systems, as will be described in greater detail below, the nozzle 36 and orifice 35 are arranged to aspirate a targeted dispensing liquid (e.g., a liquid reagent sample) into the communication passageway 33 from a reagent/sample source or source plate 38, as well as aspirate the liquid reagent sample therefrom. Unlike the current techniques, however, the present invention enables repetitive, precision low volume, non-contact liquid dispensing on the order of nanoliters without any concentration degradation of the sample due to the dispersion or dilution effect by the system fluid 40 at the liquid interface.

Referring now to FIG. 2, this is accomplished by aspirating an air gap 41 into the communication passageway, via the dispensing orifice 35, prior to aspiration of the liquid reagent sample therein. This air gap must extend continuously across the transverse cross-sectional dimension of the communication passageway to completely separate the distal end of the contained system fluid 40 from contact with the proximal end of the liquid reagent sample slug 42 drawn into the communication passageway. Since the integrity of this trapped air gap 41 is maintained between the two opposed fluids for the duration of any aspiration and dispensing operation, dispersion or dilution effects at the interface between the liquid reagent sample 42 and the system fluid 40 are substantially eliminated. That is, the air gap 41 must remain substantially intact and not fragment as the air gap reciprocate along the communication passageway 33.

Figure 5:
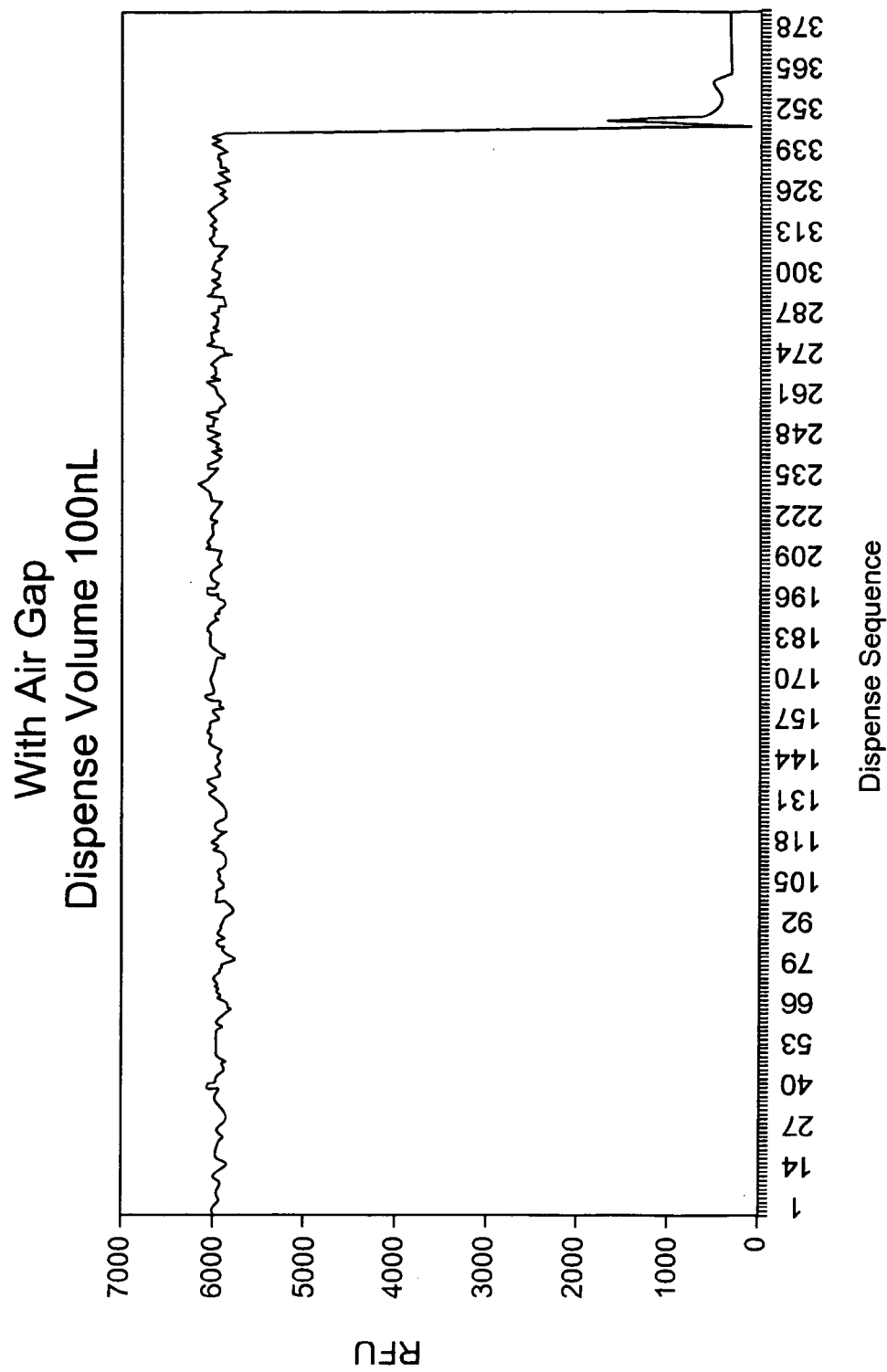
FIG. 5 is a chart illustrating the performance (measured in reagent concentration) of a sequence of 100 nl reagent dispenses utilizing the non-contact liquid dispensing system with the application of an in-line air gap, in accordance with the present invention.

Comparing the above-mentioned chart of FIG. 1, applying a solenoid-based liquid handling system without an in-line air gap with the chart of FIG. 5, applying the same solenoid-based liquid handling system with an in-line air gap, each repetitively delivering consecutive (i.e., about 350 dispenses), 100 nanoliter quantities of liquid, the performance benefits for concentration stability are clearly illustrated. Briefly, these charts illustrate the measured concentration of the dispensed liquid reagent (in Relative Florescence Units (RFU)) versus the dispense sequence. In the chart of FIG. 1, the measured concentration of the liquid sample dispense significantly degrades after the $50^{th}$–$60^{th}$ consecutive dispense due to the dispersion or dilution effect with the system fluid at the liquid interface. In comparison, the inclusion of an air gap 41 to separate the fluids significantly reduces the concentration degradation (FIG. 5) across the entire dispense sequence.

However, in order to provide precision, non-contact liquid dispensing at repetitive, substantially low volumes ranging from nanoliters to microliters, it has been found that too large of an air gap separating the liquids is detrimental to performance. For example, a 2 uL air gap can be used for replicate dispenses of 1 uL, but is too large for dispensing 100 nL. When too large a volume air gap is aspirated between the system fluid and the reagent fluid, compression of the in-line gas (air gap) can occur during a liquid dispense procedure. This compression of the air gap 41 unpredictably affects the efficiency of the pressure pulse as it traverses the air gap 41. In effect, a variable pressure drop occurs at the air gap/liquid interface instead of at the nozzle orifice. It is therefore difficult to reproduce and control the magnitude of the pressure pulse across the dispense orifice due to such added compliance in the system. Accordingly, the requisite precision and reproducibility for low volume, non-contact, liquid dispensing as low as the nanoliter range can only be achieved with air gaps in the range of 0.05–5 uL. By way of example, such compression has been observed for aspirated air gap volumes greater than or equal to about 10.0 microliters in pressure lines having a 0.020"–0.035" inner diameter for the communication passage. The air gap reacts to the pressure pulse much like a spring compressing then expanding.

In accordance with one aspect of the present invention, it has been found that aspirating smaller volumes of in-line gas significantly improve the volumetric dispensing precision and reproducibility not capable with volumes greater than about 5.0 microliters. Applying a single, continuous air gap in the range of about 250 nanoliters to about 2.0 microliters, extending across the transverse cross sectional dimension of the communication passageway, precision low volume, non-contact, liquid dispensing can be delivered from these non-contact, liquid dispensing devices while maintaining sufficient separation of the liquids at the interface to minimize dispersion and dilution by the system fluid.

Using high-speed photography, it has been observed that these discrete air gaps essentially behave as substantially incompressible fluids, unlike air gaps larger than about 10 microliters for the given diameters. Accordingly, as the pressure pulse propagates down the communication passageway (originating from the back pressure and the opening and closing of the dispensing actuator as will be described below), the pressure pulse can traverse this discrete air gap interface without significant loss of energy due to compliance. This enables greater control of the pressure pulse across the dispensing orifice 35 at the nozzle 36 for repetitive, precise, low volume, non-contact liquid dispensing in the picoliter to microliter range.

Figure 4:
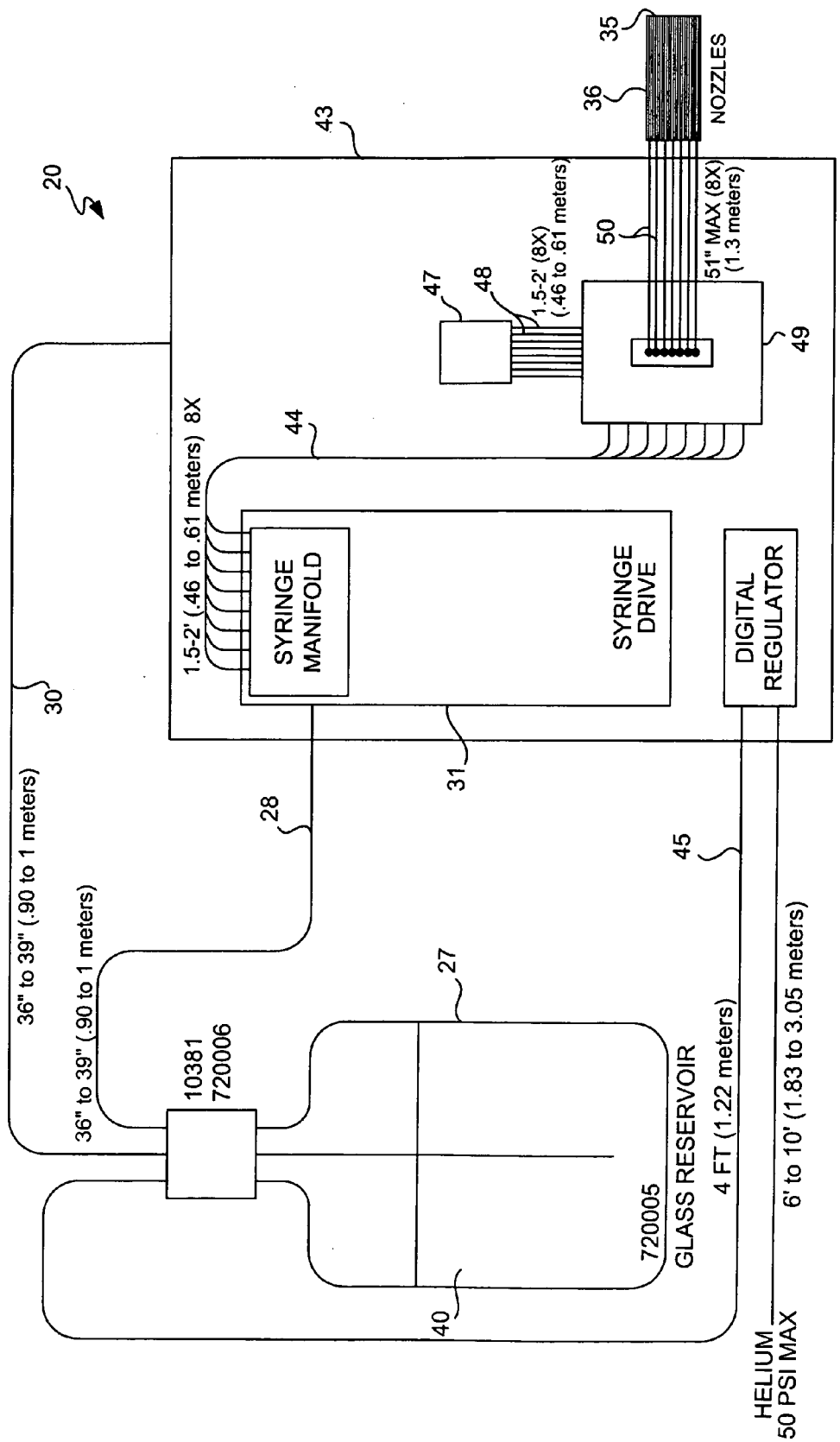
FIG. 4 is an alternative schematic diagram of FIG. 3.

Referring back to FIGS. 3 and 4, and as viewed in FIG. 6, the non-contact, liquid handling system 20 will now be described in greater detail. In the preferred form, the liquid handling system 20 is provided by multi-channel liquid dispensing device capable of simultaneous, multiple reagent dispensing from multiple nozzles 36. Similar to our UNIVERSAL NON-CONTACT LIQUID HANDLING PERIPHERAL APPARATUS, that is the subject of U.S. patent application Ser. No: 10/237,916, filed Sep. 6, 2002, the entirety of which is incorporated herein by reference for all purposes, a remote fluidic module 43 is included that houses the fluid aspiration (input) subsystem 23, the fluid dispensing (output) subsystem 25 and the fluid switching subsystem 26. The pressure subsystem 22 includes the pressurized system fluid reservoir 27, having a ⅛" pressure line 45 coupled to a digital pressure regulator 46 of the fluidic module 43. In turn, the pressure regulator 46 is fluidly coupled to a pressure source (not shown) having a maximum pressure of preferably about 50 psi. The preferred back pressure regulated by the digital pressure regulator is in the range of about 2 psi to about 15 psi, and more preferably retained in the range of about 8 psi. It will be appreciated, however, that the selected back pressure is dependent upon several factors, as will be discussed, including the parameters of the dispensing actuators, the dispensing orifice diameter and the nozzle design (creating backpressure at the orifice), the quantity to be liquid dispensed, and the viscosity of the liquid sample and system fluid. Accordingly, during operation, a constant back pressure is maintained in both the first fluid path A and the second fluid path B. It is this constant back pressure, in combination with the actuation of the dispensing actuators 32 (e.g., a solenoid dispensing valve) that creates the necessary pressure pulse to eject the drop of liquid reagent from the nozzle orifice 35.

Briefly, the pressure head at the dispensing valve 32 is created by system pressuring gas acting upon the system fluid (preferably filtered de-ionized water) at the system fluid reservoir 27. Preferably, a pressurizing gas is selected that scavenges gas bubbles in the system fluid and suppresses in-gassing and is not soluble in the system fluid. In-gassing into the system fluid can result in bubble or micro-bubble formation, and poor dispense performance caused by rapid solenoid actuation. Micro-bubbles in the system fluid, as differentiated from air gaps, will degrade dispensing performance due to pressure drops in the system. Micro-bubbles are uncontrolled and not intentionally introduced into the communication path, whereas the air gap is precisely controlled and intentional. For instance, as the pressure pulse propagates through the communication passageway 33, the cumulative effect of these micro-bubbles increases compliance that in turn, decreases the pressure drop across the dispensing orifice 35. A potential pit-fall of the out-gassing of the pressurizing gas is that air can become trapped within the previously primed solenoid. The trapped air will then create a situation where the solenoid will dispense a greater volume than it did when it was fully primed. The solenoid will open, allowing system fluid to pass valve. This will compress the trapped air within the solenoid. The system fluid has now displaced the compressed air that is trapped within the solenoid valve. As the valve is closed, the trapped air expands and pushes the system fluid that compress the air gap out of the valves.

One such pressurizing gas that is particularly advantageous is helium, when using an aqueous pressurized system fluid. This inert gas scavenges air (Nitrogen) gas bubbles in the system fluid and suppresses the formation of additional bubbles. The solubility of Helium in aqueous solutions is also less than that of air, nitrogen or argon. Accordingly, the application of helium enables the use of non-degassed, aqueous system fluids.

Incidentally, filtered de-ionized water is the most typical and benign liquid chosen as the system fluid. It will be appreciated, however, that other fluids and aqueous reagents can be substituted, depending upon the application as long as the surface tension of that fluid enables the formation of the air gap between the system fluid and the sample reagent.

Applying a 1/16"ID PFA pressure line 30, the second fluid path B is fluidly coupled to an eight (8) port manifold device 47 (FIG. 3) that distributes the system fluid into eight independent channels. More or less ports and corresponding channels may be applied, of course. In turn, each port of the manifold device 47, via pressure lines 48, is fluidly coupled to a corresponding solenoid dispensing valve 32 which in turn is fluidly coupled to a hybrid valve manifold 49 that channels fluids to the switching valve 37. These dispensing valves, which as mentioned are preferably solenoid-based, and deliver a metered pressure pulse using a pressure ranging from about $6.9(10)^3$ N/m$^2$ (1 psi) to about $138(10)^3$ N/m$^2$ (20 psi), and having a duration ranging from about 200 µs to about 10 seconds. Preferably, these dispensing valves 32 are provided by conventional ink-jet style printing valves or pumps designed for drop-on-demand printing. For instance, the Lee Company of Essex, Connecticut manufactures a solenoid-based ink-jet valve (Model No. INKX0502600AB) that is suitable for use with the present invention.

As best viewed in FIG. 3, the output of each solenoid dispensing valve 32 is directly mounted to the multiple path, hybrid valve manifold 49. The internal switching valve 37 is preferably provided by a rotary shear face valve to effect precision positioning when switching between the fluid aspiration system and the fluid dispensing system. This switching subsystem is the subject of U.S. patent application Ser. No. 09/689,548, filed Oct. 11, 2000, and entitled HYBRID VALVE APPARATUS AND METHOD FOR LIQUID HANDLING, the entirety of which is incorporated herein by reference for all purposes. Briefly, through the rotary shear face valve/hybrid manifold, the selected solenoid dispensing valves can be fluidly coupled to a selected nozzle 36.

Regarding the first fluid path A, an 1/16"ID PFA pressure line 28 extends from the system fluid reservoir 27 to the aspiration source 31 which is preferably, an eight (8) channel syringe drive, driven by a single motor drive. This multi-channel syringe drive simultaneously distributes and aspirates the system fluid into eight independent channels. This external analytical metering device, such as a syringe-based pump or a diaphragm pump, is capable of precision metered aspiration of small fluid quantities in the range of at least 250 nanoliters to about 2.0 microliters into the communication passageway of each associated pressure line 50 through the corresponding dispensing orifice 35. Typical of these aspiration devices is Model #2009D provided by Innovadyne Technologies, Inc., Santa Rosa, Calif. Similar to the solenoid dispensing valve 32, the output of each analytical syringe-based drive 31 is fluidly coupled to the associated inputs of the hybrid switching valve 37, via respective 22 gauge FEP pressure lines 44.

The output lines 50 from the hybrid valve 37 to the corresponding nozzles 36 provide the corresponding communication passageways 33 of each independent channel. Each line is preferably provided by TEFLON® (e.g. PFA\FEP) pressure tubing having sufficient flexibility to enable precision positioning of the associated nozzle 36 above either the sample source for aspiration of the sample reagent into the corresponding communication passageway, or the destination substrate surface or microtiter plate for high performance low volume dispensing thereof.

Figure 6:
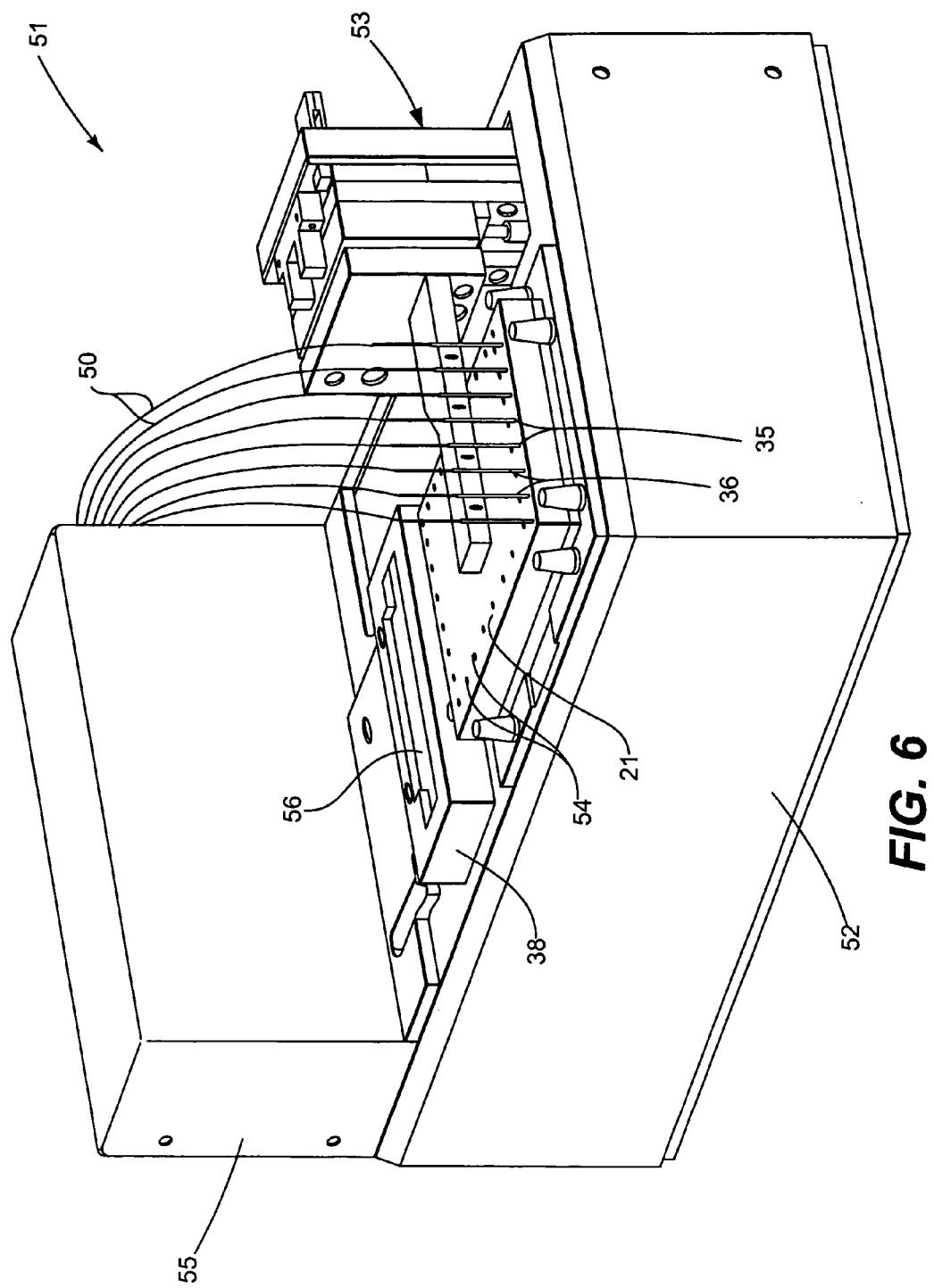
FIG. 6 is a top perspective view of a X-Y-Z "Pick and Place" mechanism utilized in combination with the present invention.

Referring now to FIGS. 3 and 6, the Universal Non-Contact Liquid Handling Peripheral 20 incorporates a "pick and place" mechanism 51 having a base 52 and an automated motion control component 53 to collectively manipulate precision positioning of the nozzles 36, as a unit. Briefly, the motion control component 53 preferably employs a conventional three-axis X-Y-Z Cartesian system, and precision track or rail hardware to position the nozzles along the X-axis and Y-axis (i.e., vertically above the targeted test sites 54 of the micro titer plate 21), and along the Z-axis. In one specific arrangement, the dispensing head provides eight (8) dispensing nozzles 36 aligned in a linear array having dispensing ends equally spaced-apart by a distance conforming to the spacing of the wells or test sites 54 of the microtiter plate 21. Other conventional positioning mechanism may also be applied, such as those having one placement component movable in the Z-axis direction above another plate component movable in the X-axis and Y-axis direction, the respective nozzles can be maneuvered above the source plate and into the targeted sample reservoir.

Further, an operation interface component 55 provides standalone or remote operation of all subsystems (e.g., the fluidics module 43 and the "pick and place" mechanism 51). More particularly, the interface component 55 operates and integrates the fluid control and motion control components. Incorporated in this chassis are all of the printed circuit boards, connectors, and firmware required to operate the instrument. Software may reside on a host computer independent of the interface component.

The hybrid valve apparatus and the non-contact liquid dispensing peripheral are adaptable for printing arrays wherein the distance between adjacent test sites 54, or test site pitch, is in the range of about 1 micron (em) to about 10,000 microns (μm). Thus, the present invention is particularly suitable for transferring chemical or biochemical samples or reagents from the sample source plate 38 having an array of reservoir wells 56 (e.g., a conventional microtiter plate with 96 or 384 wells) to an array of higher-density test sites 54 (e.g., a 1536-well microtiter plate), or for fabrication of a chip-based biological sensor (commonly referred to as a "microarray") used for performing gene expression or other screening experiments. The source plates are generally used in sample analysis protocols, and are typically provided by plastic plates defining uniformly spaced depressions or wells (i.e., test sites 54) that contain the fluid dispensing therein. These commercially available rectangular plates further typically include eight rows of twelve microwells that provide an industry-standard ninety-six microwell plate, such as plate 21 shown in FIG. 6. Other conventional sizes include sixteen rows of twenty-four microwells that provide three hundred eighty-four microwells.

Referring back to the TEFLON (PFA\FEP) pressure lines 50, these elongated, chemically inert lines are selected to perform functions other than merely providing the respective fluid communication passageway 33 between the hybrid valve outlet and the respective nozzles orifice 35. For example, to further reduce in-gassing, the lines can be selected to be substantially chemically inert to biological fluids and commonly used solvents, such as DMSO, THF, alcohols, aldehydes, ketones, halogenated hydrocarbons, aliphatic hydrocarbons, acids and bases used in the life sciences and diagnostic fields. These pressure lines must also be sufficiently flexible to enable X-Y-Z positioning of the nozzles 36, which are mounted to the X-Y-Z "pick and place" mechanism 51 (FIG. 6). Further, the remote placement of the solenoid actuators 32, relative the nozzles 36, allows for enhanced flexibility in designing the dispensing systems. That is, several factors are considered when selecting the overall length of the pressure lines 50, as well as the internal diameter of the communication passageway.

Although the length of the pressure line 50 is a factor in determining the sum volume of the communication passageway 33, to be discussed later, it has been found desirable to position the in-line air gap 41 sufficiently downstream from the solenoid dispensing actuator 32 in order to maintain the integrity of the air gap 41 across the transverse cross-sectional dimension of the communication passageway. Depending upon the back pressure at the system fluid reservoir 27, should the air gap 41 be positioned too close to the solenoid dispensing actuator 32, the initial shock or impact from the pressure pulse propagating down the communication passageway 33 may be sufficient to fragment the air gap. Since the volume of the air gap 41 is very minute (i.e., about 250 nanoliters to about 2.0 microliters), dilution and dispersion of the opposed liquids at this interface is likely with any fragmentation.

Accordingly, by lengthening the pressure lines 50 by a sufficient amount in addition to the targeted cumulative volume of liquid reagent sample aspirated into the communication passageway 33, the air gap 41 can be positioned sufficiently downstream from the dispensing actuator 32 so that the system fluid volume 40 in the passageway 33 partially isolates and cushions the impact of the pressure pulse on the air gap 41. Moreover, it is believed that the flexibility of the pressure lines 50 themselves help dampen the initial impact of the pressure pulse through motion absorption as the flexible pressure lines moves and flexes upon initial entrance of the pressure pulse in the communication passageway 33. By way of example, for a flexible pressure line having an internal diameter in the range of about a 0.020"–0.035"ID, a back pressure in the range of about 2 psi to about 15 psi, and an air gap 41 of about 250 nanoliters to about 2.0 microliters, the air gap 41 is preferably positioned downstream from the entrance into the communication passageway in the range of at least 1.0 inch to about 3.0 inches.

Another consideration when selecting the pressure lines 50 and corresponding fluid handling components is maintaining the integrity of the minute air gap 41 as it reciprocates in the communication passageway 33. This is primarily performed by providing relative smooth wall transitions within the communication passageway 33. Such smooth transitions are critical to preventing fracture of the air gap 41 as it moves through the communication passageway. This holds especially true at any component interface, such as between the pressure line 50 and the nozzle 36. Abrupt transitions, such as stepped transition from a larger diameter to a smaller diameter or protruding objects from the interior walls, may impact the integrity of the air gap as it passes by. Accordingly, a significant effort is afforded to match the properties of the components to smooth all transitions, especially component interfaces. Operations such as electrochemical polishing of the Stainless Steel probes and beveling of the Stainless Steel tube that connect the nozzle to the fluid line can minimize dispersion effects caused by stepped transitions. Controlling the dimensions of all the fluid lines and channels helps to enhance performance and reduce imprecision.

Other factors influencing fluid dispensing include the interior diameter of the communication passageway, the back pressure created by the nozzle design (e.g., straight or angled passageway) and orifice diameter, the viscosity of the liquid reagent fluid to name a few. In still other considerations, as indicated, the length of the pressure line 50 can be tailored to the targeted dispense application. Generally, in accordance with the present invention, the smaller the quantity of fluid to be dispensed for these non-contact fluid dispensing systems 20, the shorter the length requirements of the pressure lines, whereas, the greater the quantity of low volume fluid dispensing, the longer the length requirement, outside of the mere volume considerations of the communication passageway.

By way of example, for a smaller quantity of liquid dispensed (e.g., 50 nl), the length of the pressure line should be preferably reduced to maintain the requisite pressure drop across the nozzle orifice 35 that is necessary to eject the drop cleanly in these minute volumes. This is due in part because the solenoid dispensing valves 32 are required to operate within an optimum back pressure range to assure proper performance. Too low a back pressure will not be sufficient to cleanly eject the drop from the nozzle orifice, while too high a back pressure will prevent proper operation of the valve (e.g., preventing opening of the valve at all). The optimum back pressure range for most solenoid dispensing valves 32 in this category is from 4 psi to about 15 psi.

However, to effect smaller dispensing quantities, smaller pulse widths are required, resulting in an overall lower pressure. Too long a length pressure line will likely cause too small of a pressure drop across the orifice 35 since such a drop is a function of the pressure line length. That is, the longer the pressure line length, the greater the pressure drop due to the incremental pressure loss caused by friction between the interior wall and the fluid. Although the trapped air and dead volume within the solenoid valve 32 and communication passageway 33 are preferably purged, as will be detailed in the purge routine described below, to reduce compliance within the system, there are still pressure losses due to the friction of the fluid with the walls of the pressure line. Too small a pressure drop across the orifice causes reduced ejection volumes, given the same pulse width and fluid reservoir back pressure. Consequently, residual sample fluid may build-up at the orifice 35 during subsequent ejections until one particular ejection carries this build-up in the ejected drop, significantly increasing the dispensing volume. This of course results in volumetric imprecision and variance. For longer pressure line lengths, in comparison, greater quantities of low volume dispensing are delivered accurately by adjusting the back pressure or pulse width to achieve the requisite pressure drop for clean ejection of droplets.

As an example to this aspect of the present invention, to effect about a 50 nl fluid dispense, with a back pressure nominally at about 8 psi, the length of the pressure line, having an interior diameter of about 0.028 inch nominal, should be in the range of about 2.0 inches to about 12 inches. In another example, for a 200 nl fluid dispense, using the same system pressure, the length of the pressure line 50 should be about 2.0 inches to about 118 inches (3 meters). Generally, with longer tube lengths, either the pulse width or the back pressure must be increased, relative to the shorter tube length, to deliver an equivalent amount of fluid. This is provided that the viscosity of the fluid remains unchanged.

Depending upon the predetermined volume to be aspirated into communication passage, which incidentally is predicated upon the cumulative volume of repetitive dispensing from the nozzle (to be discussed), the length of the pressure line 50 and the inner diameter thereof may be determined. Using long-tube, remote dispensing with from about 5.0 inches to about 120.0 inches of about 0.020 inch ID to about 0.035 inch ID tubing between the nozzle orifice 35 and the solenoid based actuator 32 (FIG. 2, volumes of 25 nanoliters to 70 microliters can be dispensed with a dispense performance of less than 5% Relative Standard Deviation (RSD). By way of example, applying the present inventive method of aspirating minute air gaps between the fluids, such length fluid communication lines 50 having a 0.028" nominal internal diameter, can yield about two-thousand (2000) to about forty-four thousand (44,000), 25 nanoliter volume dispenses each having substantially equal concentrations (comparing FIG. 1 (the system application without a minute air gap) to FIG. 5 (the system application with an air gap)). To illustrate scalability, this approach can also yield about one (1) to about twenty-five (25), 40 microliter volume dispenses as well. In other examples, using a single 500 µl aspirated volume, about forty-eight hundred (4800), 100 nanoliter dispenses to about four-hundred eighty (480), 1 microliter dispenses with substantially equal concentrations can be attained having an RSD less than 5%. Variations include systems where the tubing diameter varies form 0.010" ID to 0.040" ID; tubing length greater than 120" with RSD less than 10%.

Application of the present inventive technique will now be more fully described. Referring to FIG. 2, prior to aspirating the minute air gap 41 into the communication passageway, the system fluid 40 in each communication line 50 must be maneuvered to the end of the corresponding dispensing orifice 35 regardless of which hydraulic state the system is in (e.g., dry, partially dry or wet hydraulic state). Applying the backpressure of the system fluid reservoir, this may be performed either through the solenoid dispensing valve 32 (second fluid path B) or the syringe-based aspiration actuator 31 (first fluid path A), or both.

Regarding the second fluid path B, the switching valve 37 is oriented to enable fluid communication between the solenoid dispensing valves 32 and the corresponding communication passageways 33. The solenoid dispensing valve 32 can then be operated from a closed condition, preventing or closing fluid communication between the communication passageways and the corresponding solenoid dispensing valves 32, to an opened condition, enabling or opening fluid communication between the communication passageways and the corresponding solenoid dispensing valves 32. The constant back pressure of the pressurized system fluid reservoir 27 is then applied to the system fluid for flow thereof through solenoid and into the communication passageway 33. This is performed until the system fluid is dispensed from the corresponding dispensing orifices 35 in a substantially constant and bubble free manner. A trapped gas purge routine may then be applied which will be described in greater detail below.

Similarly, regarding the first fluid path A, the switching valve 37 is oriented to enable fluid communication between the syringe-based aspiration actuator 31 and the corresponding communication passageways 33. A three-way valve in the syringe drive can be opened to enable fluid communication between the communication passageways and the system fluid reservoir. Again, the constant back pressure of the system fluid reservoir 27 or the priming action of the syringe drive can be applied to flow the system fluid through the channels of the hybrid valve and the corresponding communication passageways 33 until exiting the system in a manner substantially constant and bubble free.

Once the system fluid is satisfactorily moved all the way to the end each dispensing orifice 35 and any trapped gas is deemed purged from their respective communication passageway and solenoid dispensing valve 32, as will be described, the nozzles 36 may be positioned vertically over the respective wells of the source plate 38, via the "pick and place" mechanism 51, prior to aspiration of the respective reagent sample. With the hybrid valve 37 positioned to enable fluid aspiration, each corresponding precision analytical syringe drive 31 is operated to accurately meter air, as a unit, into the communication passageway 33, via dispensing orifice 35. In accordance with the present invention, this separating volume ranging from about 150 nl to about 5 µl, and more preferably about 250 nl to about 2 µl.

Applying an X-Y-Z "pick and place" mechanism 51, such as that Universal Non-Contact Liquid Handling Peripheral 20 above-mentioned, the respective nozzles 36 can be maneuvered into the targeted sample reservoir. Subsequently, actuating the corresponding precision analytical syringe drive 31, a single continuous slug of the reagent fluid sample is drawn into communication passageway. Preferably, the minute air gap 41 is maintained within the communication passageway 33 of the associated tube, and is not drawn into the hybrid valve 37. While the air gap 41 may be positioned upstream from the hybrid valve 37, it is preferable to retain the air gap downstream from the hybrid valve 37, and maintain the minimum downstream distance from the solenoid dispensing valve by merely lengthening the corresponding pressure lines 50. As indicated above, the length and ID of the lines are selected as a function of the volume predetermined to be aspirated into the communication passage.

The hybrid valve 37 is operated to switch the respective communication passageways 33 from communication with the corresponding analytical syringe drives 31 to the corresponding solenoid dispensing valves 32 remotely located on the fluidics module. Applying the abovementioned techniques and the "pick and place" mechanism should be 51, the nozzles 36 are repositioned above their destination test sites 54. The solenoid-based actuators 32 are precisely actuated between the closed condition to the opened condition to control the pulse width (i.e., the length of time the valve is opened) to determine the volume of the drop ejected from the corresponding nozzle orifice. As mentioned above, and using the calibration techniques to be discussed below, the pulse width corresponding to volume liquid reagent ejected from the orifice is a function of many factors, including the viscosity of the liquid reagent sample, the length of the lines 50, the ID of the line, the back pressure of the system fluid reservoir, the resulting back pressure across the nozzle orifice which is a function of the nozzle design. For example, to effectively dispense a solution such as 30% Glycerol/water, a higher back pressure is required, a longer pulse width is required, and slower aspirate speeds must be used relative to performing a dispense of a less-viscous solution such as Hexane. The ability to empirically calibrate a variety of fluids, through the use of fluorescent labeling or gravimetric measuring, enables the development of a matrix of compound classes that can be referenced by the instrument to use as offsets from a pre-determined calibration.

In accordance with another aspect of the present invention, a method has been developed to purge trapped air within the solenoid based actuators 32 when the system fluid is initially flowed through the actuators and the communication passageways from a dry air-filled state to a wet hydraulic state. As mentioned, the purging of such trapped gases is imperative for precise, non-contact, liquid dispensing at these low volumes. Each trapped air bubble or micro-bubble in the solenoid itself, and those adhered to the walls of the communication passageway 33, as compared to the minute air gap 41 traversely extending the entire communication passageway, micro-dampen the pressure pulse propagating down the communication passageway. The collective influence of this compliance in the system, however, results in a significant system pressure loss resulting in an ineffective pressure drop across the nozzle orifice 35 that can reduce volumetric precision. Also, the spring like contraction and expansion of the bubbles causes imprecise dispensing.

Using repetitive fixed pulse solenoid actuations, a "buzz" routine has been developed to dislodge the trapped gases in the dispensing actuator and corresponding communication passageway 33 of the pressure line 50 that are ultimately purged out from the nozzle orifice. Applying fast actuations, opening and closing the dispensing valve at high frequency bands, together with the back pressure of the system fluid reservoir, the routine effectively purges or expels bubbles or air trapped in the solenoid valves. Since relatively high frequencies actuations in the range of 1 Hz to about 1700 Hz are applied, coded firmware is thus required to properly perform the routine. More preferably, the frequency range of about 10 Hz to about 420 Hz are utilized.

It has been found particularly effective to vary the solenoid actuation frequency to assure complete purging of the trapped bubbles. Depending upon the amount of trapped gas within the solenoid, the different frequencies of the actuation are effective in dislodging the gas within the solenoid. The consequently reduced compliance of the purged solenoids, has great impact on the performance of multiple solenoid systems, greatly improving dispense precision and stability of multi-channel systems. For example, one (1) to twenty-five (25) discrete frequency bands can be applied in a random frequency range from about 10 Hz to about 420 Hz. In another specific embodiment, as shown in the Table I of FIG. 7, a fixed pulse ramped frequency increase sweep from about 1 Hz to about 420 Hz over one (1) to fifteen (15) discrete, equally-spaced frequencies. Thus, it is the different discrete frequency bands that has been found effective, although certain delivery patterns may be even more effective. By way of example, one routine may include a ramped frequency decrease sweep, with denser frequency spacings at the higher or lower frequencies. Briefly, the actual actuation frequency in the fourth column of Table I of FIG. 7 is not linear at the higher nBuzzCount rate since the execution of the each actuation command takes about 200 us. At the relatively low frequencies, this is not much of a factor but it becomes a factor with higher repetitions.

In a multiple channel system, such as in our Universal Non-Contact Liquid Handling Peripheral Apparatus, above-mentioned, simultaneous purging of the communication passageways 33 can occur through simultaneous actuation of the corresponding solenoid dispensing valves 32 coupled thereto. However, not all solenoid dispensing valves and their associated communication passageways will be purged equally and at the same rate. According, a technique has been developed to determine the quality of the purge in all pressure lines after completion of the "buzz" routine.

This is performed by generating a pressure pulse through each corresponding solenoid dispensing valve, each of which has substantially the same pulse width. Essentially, an attempt is made to dispense substantially equal volumes of system fluid independently from each pressure line. The liquid dispensed from each respective nozzle orifice is collected to determine the dispensed volume. Conventional measuring techniques can be employed, such as by weighing, spectrophotometric, or optical methods. For example, applying a back pressure of approximately 8 psi, operating the solenoid dispensing valves 32 to generate a twenty-eight thousand (28,000) µs pulse width should typically yield about a thousand (1000) nanoliters of system fluid.

Applying these measured volumes of dispensed liquid, the mean variance is calculated. For any of the pressure lines 50 that delivered a fluid amount having a measured volume that exceeds the mean variance by an amount greater than a predetermined figure, trapped gas may still remain in the solenoid actuator and/or the communication passageway. Thus, this continued compliance is the cause of such measured difference from the mean variance. In one specific embodiment, the predetermined figure is in the range of about 3% to about 7% difference from the calculated mean variance, and more preferably about 5%. Variance is the percent difference of the average for a single tip compare to the mean of the dispenses for all of the tips, as set forth herein:

% Variance=((Tip mean−Mean of all tips)/Mean of all tips)*100.

To address these differences, the purge routine for those particular lines or the entire set of lines is repeated, and the dispense sequence and volume measurement is repeated. In fact, this entire procedure is repeated until each line delivers fluid quantities that differ from the mean variance within the predetermined figure. Once the variance is within specifications all pressure lines 50 and their associated solenoid dispensing valves have been properly purged of trapped bubbles and are hydraulically intact.

In still another aspect of the present invention, an apparatus and technique has been developed to monitor the flow or lack of flow through the dispensing orifices 35 in each respective nozzle 36. Since the nozzle or dispensing orifices 35 are relatively small, in a range of preferably about 50 microns to about 250 microns, plugged dispensing orifices are an inherent problem in these low volume dispense systems. Thus, a plug detection sensor assembly, generally designated 70, is applied to detect "plugging" of the orifice 35. As best viewed in FIGS. 9 and 10, the sensor assembly 70 is mounted at the tip of the nozzles 36 which are carried by the automated motion control component 53 of the "pick and place" mechanism 51. Preferably, the sensor assembly is provided by an optical "through beam" sensor having an optical beam emitter component 71, emitting an optical beam, and a receiving component 72, sensing the optical beam. Alternative optical device variations may be employed however.

By placing and aligning the components of the sensor assembly 70 just downstream from the dispensing orifice 35, any flow of liquid dispensed from the dispensing orifice 35 will impair the transmission of the beam of light from the optical emitter component 71 to the receiving component 72. Accordingly, proper ejection of dispensed liquid from the nozzle orifice 35 will impair passage the beam of light, indicating that the integrity of the dispensing orifice has not be compromised, and that proper operation can commence. Moreover, since these low volume liquid dispensing systems typically eject micro-droplets of liquid from the dispensing orifice 35, as opposed to a continuous stream of liquid, the breakage from continuous receipt of the light beams are on the order of milliseconds. Once the droplet has passed, the light beam is again received and detected by the receiving component 72. By way of example, for the passage of a about 50 nanoliter liquid dispense, applying a system fluid back pressure of approximately 8 psi, the breakage of the beam is only on the order about 2–3 ms.

In contrast, should the respective nozzle orifice 35 be completely clogged, the breakage of the beam will not occur, indicating a potential problem. In more sophisticated operations, where larger volumes are to be dispensed from the nozzle orifice 35, partial clogged orifices may be detected. For instance, for a predetermined dispensing volume of a known liquid, and known hardware and parameters (e.g., system fluid back pressure, orifice diameter, exit velocity, etc.), the time required to break the beam may be known or estimated. However, should the break in the beam be of a period significantly less than the known or estimated period, although a break does occur, a partially clogged orifice may be detected.

Figure 10:
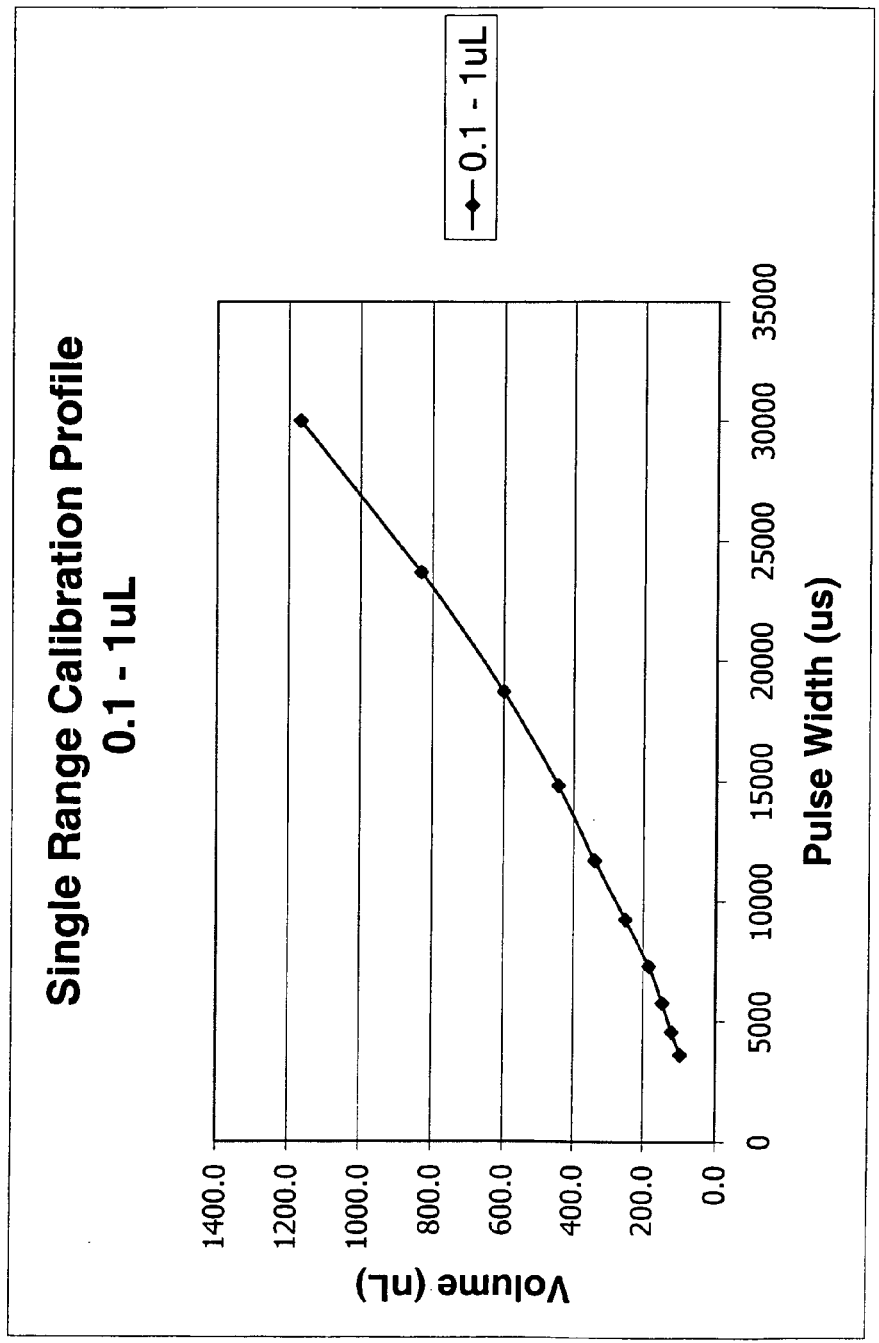
FIG. 10 is a graph of a Calibration Profile for dispense volumes ranging from 0.1 microliter to 1.0 microliter constructed in accordance with the calibration technique of the present invention.

In one configuration, each nozzle 36 may include a dedicated sensor corresponding to each nozzle orifice 35. Such an arrangement would of course be substantially more costly. In another specific embodiment, as illustrated in FIG. 10, the sensor components 71, 72 of the sensor assembly 70 are preferably placed in-line, longitudinally, with the array of nozzles 36 so that only one sensor is required. In this arrangement, the optical emitter component 71 is placed outboard from one end of the nozzle array while the receiving component 72 is placed outboard from the other opposite end of the array. Thus, the optical emitter can emit a light pulse across the entire array (e.g., 6–12) nozzles orifices 35 such that the ejection of a drop of liquid from any one of the orifices will impair detection of the light beam by the receiving component 72.

In this approach, each individual channel must of course be monitored independently when detecting flow or lack of flow through the corresponding orifice 35. The firing and detection sequences can be in any order, as well as any clog or partial clog detections can be determined, controlled and operated using sensor hardware and associated with the software/firmware code, data acquisition, fault determination, algorithms and recovery protocols that respond to the acquired data.

The optical emitter component 71 of the optical sensor assembly 70 is preferably provided by a laser diode or the like. The optical receiving component 72 is of course selected to detect light in the wavelength range transmitted by the diode. For example, the laser diode may be selected to transmit light in the visible range which is beneficial in that these are safe wavelengths, and use inexpensive components. One such optical sensor suitable for this application is the Sun-X Optical Sensor (Model No. FX-D1), manufactured by SUNX of Nagoya, Japan.

To facilitate detection of the light beam transmitted across the nozzles, it may be necessary to decrease the intensity of the light beam emitted by the diode. When the emitted light received by the receiving component is too intense, the beams essentially pass through the drop, especially when substantially transparent, alluding detection. Decreasing the light intensity, in effect, yields an overall increase in the detection sensitivity so that the ejected drops become more "visible" to the receiving component.

One technique applied to reduce the light beam intensity sensed by the receiving component 72 is to position a diffuser or filter 73 in front of the face of the receiving component. This is accomplished by covering the face of the receiving component 72, and providing a small aperture 74 that reduces the amount of light transmission through to the receiving component. Preferably, the aperture is in the range of about 0.005 inch to about 0.030 inch in diameter, and more preferably is about 0.020 inch in diameter. Other arrangements that reduce the light intensity received by the receiving component include optical filters.

The sensor assembly 70 includes a pair of brackets 75a, 75b (FIG. 10) that enable mounting to the motion control unit 53, relative the dispensing orifices 35 of the nozzles 36. These mounting brackets 75a, 75b are arranged to face the corresponding optical components 71, 72 inwardly toward one another for transmission and receipt of the light beam. In one configuration, the transmission face of the optical emitter component 71 and the receiving face of the receiving component 72 are preferably positioned in the range of about 0.25 inch to about 2.0 inches downstream from the corresponding end nozzle orifice 35, and more preferably about 0.75 inch downstream therefrom. Further, each component face is preferably positioned in-line along the longitudinal axis of the array of nozzle orifices 35, but laterally spaced outboard from the corresponding end nozzle orifices about 0.25 inch to about 2.0 inches, and more preferably about 0.75 inch. These brackets 75a, 75b, may also provide adjustments to enable fine tuning of the position of the sensor components.

In another aspect of the present invention, a method is provided for calibrating the volume dispensed from these low volume, non-contact, liquid dispensing systems 20 before application of the present inventive dispensing methods. As mentioned, these systems rely upon pressurized fluids and micro-dispense (solenoid) valves to generate fluid flow through the communication pathways and ultimately the dispensing orifices 35. Unlike conventional syringe-based pump technologies, system configurations, reagent fluid properties and environmental conditions significantly contribute to the flow output and the dispensed volume from the system, as will be discussed. Conventional syringe pump technologies, for instance, use mechanical drives to fill and empty a syringe. Generally, regardless of the fluid properties, system design and environmental conditions, the volume of fluid filled into and dispensed from the syringe in these systems is directly proportional to the number of steps that the syringe drive is commanded to move.

Periodically, the syringe drive may be calibrated to evaluate the accuracy and precision of these mechanical pumps. It is not possible to adjust these stepped drives to improve accuracy, instead the drive must be commanded to move a different number of steps other than the theoretical number of steps to achieve accuracy. For example, this may be determined by the following equation:

Volume (steps)=(Volume desired)(Total number of steps per full stroke/syringe volume)(e.g. 750 Volume (steps)=250 uL (15000 steps/500 uL)=7500 Steps).

The technology applied in solenoid-based dispensing valves 32 is very different from that of the positive displacement syringe pump. As indicated-above, the solenoid dispensing valves 32 and the pressurized system fluid reservoir 27 of the liquid dispensing system 20 cooperate to perform liquid dispensing by actuating the dispensing valve from closed condition to the opened condition for various time periods to deliver different volumes of liquid reagent sample to the destination site. The volume of liquid dispensed from the dispensing valves is proportional to the length of time that the valve is held open. The dispensing volume from these systems is, thus, dependant upon several factors including: the time the valve is opened; the back pressure of the system fluid; the diameter of the dispensing orifice; and the distance between the micro-dispense valve and the tip (i.e., the friction between the fluid and the walls of the pressure lines). Accordingly, the numerous variables that are involved make mathematically calculating the dispense volume, based upon the length of time of valve is opened, extremely laborious and difficult for such high precision low volume liquid dispensing instruments.

A universal calibration technique has therefore been developed to estimate the dispense output from for these low volume, non-contact, liquid dispensing systems 20 that may be applied for every hardware configuration (e.g., tube length, orifice diameter, tip design, etc), reagent solution property and environmental condition. This same calibration technique can be applied to calibrate or tune these non-contact liquid dispensing systems to dispense desired volumes (in the range of about 0.05 μL to 50 μL), irrespective of the hardware configuration or the solution properties. Thus, while the implementation of this calibration technique is not dependant on these variable parameters, such as valve open time, system fluid back pressure, orifice diameter or tube length, etc., the Calibration Profile generated from these measured quantities is dependant upon such above-mentioned parameters. That is, the calibration technique is not dependent on any variables, but the result (the actual dispense volume) is dependant on the variable mentioned.

Accordingly, this calibration technique must be performed for every hardware configuration, and for every reagent liquid that will be dispensed from that particular hardware configuration. Briefly, when the same hardware configuration and liquid reagent sample is to be dispensed from each orifice of these multi-channel liquid dispensing systems, this calibration technique may be performed systematically, and then averaged for each channel. In other instances, however, where channels may have different hardware configurations, and where different liquid reagent samples of varying dispense volumes may be dispensed, then this calibration technique may be performed per each individual channel. Other environmental factors such as temperature may also affect the Calibration Profile. To insure proper performance it is desirable that a calibration be performed at the site where the instrument will be used.

In accordance with the present inventive calibration technique, a Calibration Profile is to be generated graphing the dispense volume as a function of the pulse width (i.e., the open time of the solenoid valve 32). An example of this is the Calibration Profile of FIG. 10 together with the Table II of FIG. 11, illustrating the dispense volume (e.g., nanoliter) vs. the pulse width (e.g., microseconds). For a dispense volume range of about 0.1 microliter to about 1 microliter, ten calibration points have been selected to generate the Calibration Profile. However, it is possible to use less calibration points or more calibration points. Disregarding practicality, the greater the number of points, the greater the accuracy of the Calibration Profile that is generated. Typically, once the target range of volume to be dispensed is determined for a particular dispensing session or procedure, calibration points should at the very least be selected to be below the lower base pulse width and above the upper ceiling pulse width. Table II of FIG. 11, by way of example, shows the lower base pulse width of 3,600 microseconds and the upper ceiling pulse width of 30,000 microseconds to bracket the range of 0.100 μL to 1.00 μL. Several intermediate points should then be selected within the targeted volume range of liquid dispensing as well, one technique of which will be exemplified below. Other than through experience and educated estimates, the pulse widths required to dispense liquid volumes less than the lower base width, and greater than the upper ceiling pulse width for the targeted range of volumes are estimated.

In the example of FIGS. 10 and 11, for a pressure line of about 51 inches in length, a dispensing fluid density of about 0.9977735 g/mL, a back pressure of about 8.00 psig and an ambient temperature of about 23° C., a pulse width of 3600 microseconds has been selected to dispense a volume of the reagent liquid below the lower base volume range of 0.1 microliter. Inputting a pulse width of 3600 microseconds into the operation interface component 55 of the liquid dispensing system 20 essentially opens the solenoid valve for this time period. Incidentally, these solenoid dispensing valves above-mentioned may be precisely actuated open for periods as small as about 300 microseconds. While the minimum spike actuation time at the spike voltage of 24 Volts is 250 microseconds for these valves, 200 microseconds actuations are attainable in combination with a crystal clock frequency of 20 microseconds.

The dispensed volume is collected, and then measured to determine the actual volume dispensed. Briefly, as will be described in greater detail below, two low-volume measuring techniques are applied in connection with the present invention. One low volume measuring technique involves weighing the dispensed fluid (i.e., gravimetric technique), while the other involves measuring the Relative Fluorescent Units (spectra-photometric technique) of the low dispensed volumes. There are many detection techniques such as absorbance, luminescence, and mass spectrometry that can be used. Differing detection techniques allow a broad range of chemistries to calibrated. Regardless of detection technique, multiple replicate pulses at a single pulse width are delivered, measuring the average dispensed volume. Such averaging reduces any errors in accuracy that would be caused by variances in precision from each individual dispense. Moreover, for multi-channel applications having identical hardware configurations, etc., as above-indicated, systematic calibration can occur averaged by the number of channels.

Once the average dispensed volume is measure and calculated, which for the initial pulse width of 3600 microseconds is about 0.097 microliters, the calibration point along the Calibration Profile can be plotted. Essentially, the measured volume delivered can be correlated to the open valve time (i.e., the pulse width). Applying more points, as illustrated in Table II of FIG. 11, the Calibration Profile of FIG. 10 can be generated for the volume range of 0.1 microliter to about 1 microliter for this particular hardware configuration. Once this is established, any dispensing volumes within this target volume dispensing range may be delivered through interpolation techniques with accuracy in the range of about −5% to about +5%. Further, through the operation interface component 55 which incorporates the necessary software/firmware code, data acquisition, fault determination, algorithms and recovery protocols that respond to the acquired data, the delivery volumes can be automated.

For low volume, non-contact liquid dispensing in the very low volume ranges attainable through the application of solenoid dispensing valves 32, where the valve openings (i.e., the pulse widths) are controlled in the (200 microseconds=0.2 milliseconds) microsecond range (i.e., $1 \times 10^{-6}$ seconds), the selection of the calibration points is critical. Generally, at commencement of flow through the solenoid dispensing valve 32, the flow velocity increases until a maximum flow is reached. In this range, the rate of change of the flow of reagent (i.e., acceleration) through the valve is increasing and the flow is thus not steady-state. Once maximum velocity is attained, the flow is substantially not changing where the rate of change of the flow (i.e., acceleration) is substantially zero. The dispense profile, thus, becomes linear.

Figure 12:
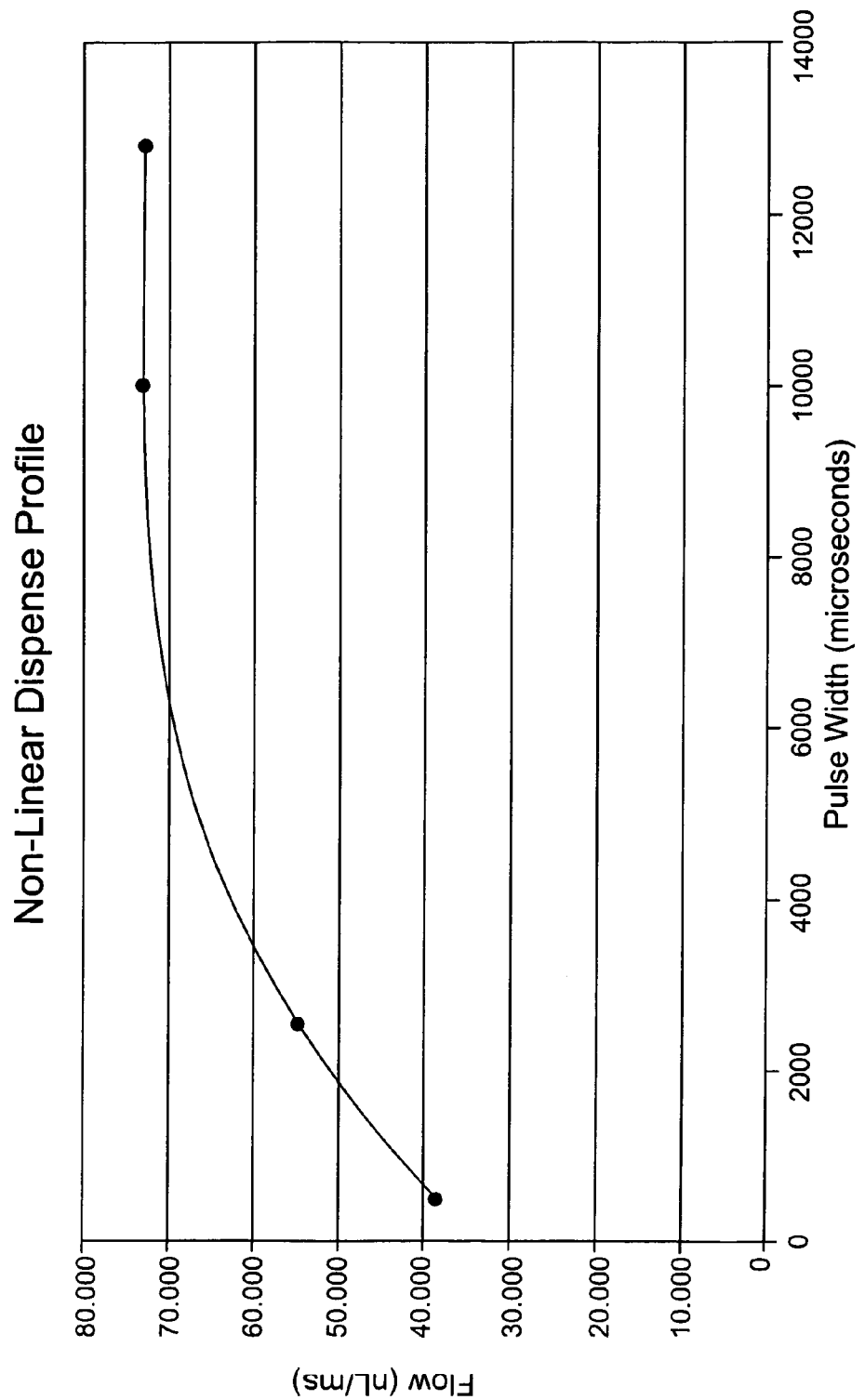
FIG. 12 is a graph of a Non-Linear Dispense Profile illustrating transient and static flow through the dispensing valve correlating to the open valve time (i.e., the pulse width).

This is exemplified more clearly in the Dispense Profile graph of FIG. 12, correlating the flow (nanoliters/millisecond) vs. the pulse width (microseconds). Viewing the Dispense Profile graph is perhaps more intuitive than viewing the Calibration Profile of FIG. 10 where the inflection region or point can be seen where the flow becomes substantially steady somewhere between about 8,000 microseconds to about 10,000 microseconds, in this instance. Experience has shown that maximum flow velocity typically occurs approximately at dispensing volumes in near to 0.5 microliter for a wide variety of hardware configurations, solution properties and ambient conditions.

Due to the non-linear, non-steady-state, fully developed, laminar nature of flow until maximum flow velocity is reached, it is this transient region that is more difficult to profile. Accordingly, the majority of the calibration points should be established within this (nonsteady-state, fully developed, laminar) region. Thus, a greater number of pulse width selections should be allotted in this region when constructing the Calibration Profile (FIGS. 10 and 12). In contrast, in the more linear region of the dispense profile where the flow is substantially steady, fewer calibration points are required determined to interpolate the Calibration Profile. It will be appreciated, however, that consideration of the transient flow is more imperative at very low volume dispensing (between about 0.10 microliter to about 1.00 microliter), and at very short pulse widths (in the range of about 3,000 microseconds to about 10,000 microseconds). In contrast, when the target dispense volume is to occur where the flow velocity is at maximum velocity, such transient flow need not be considered because the fluid is no longer accelerating.

When target delivery volumes span a substantially wide range of volumes (e.g., from about 0.1 microliter to about 50.0 microliters), the calibration profiles may be separated into discrete narrowly defined volume ranges (i.e., three or more Calibration Profiles traversing or overlapping different volume ranges). Subsequently, these profiles can be combined into one composite Calibration Profile. In Table III of FIG. 13, for example, the volume ranges are separated into three different volume ranges: 0.1 microliters to 1.0 microliter, 1.0 microliter to 10.0 microliters and 10.0 microliters to 40.0 microliters.

Figure 14:
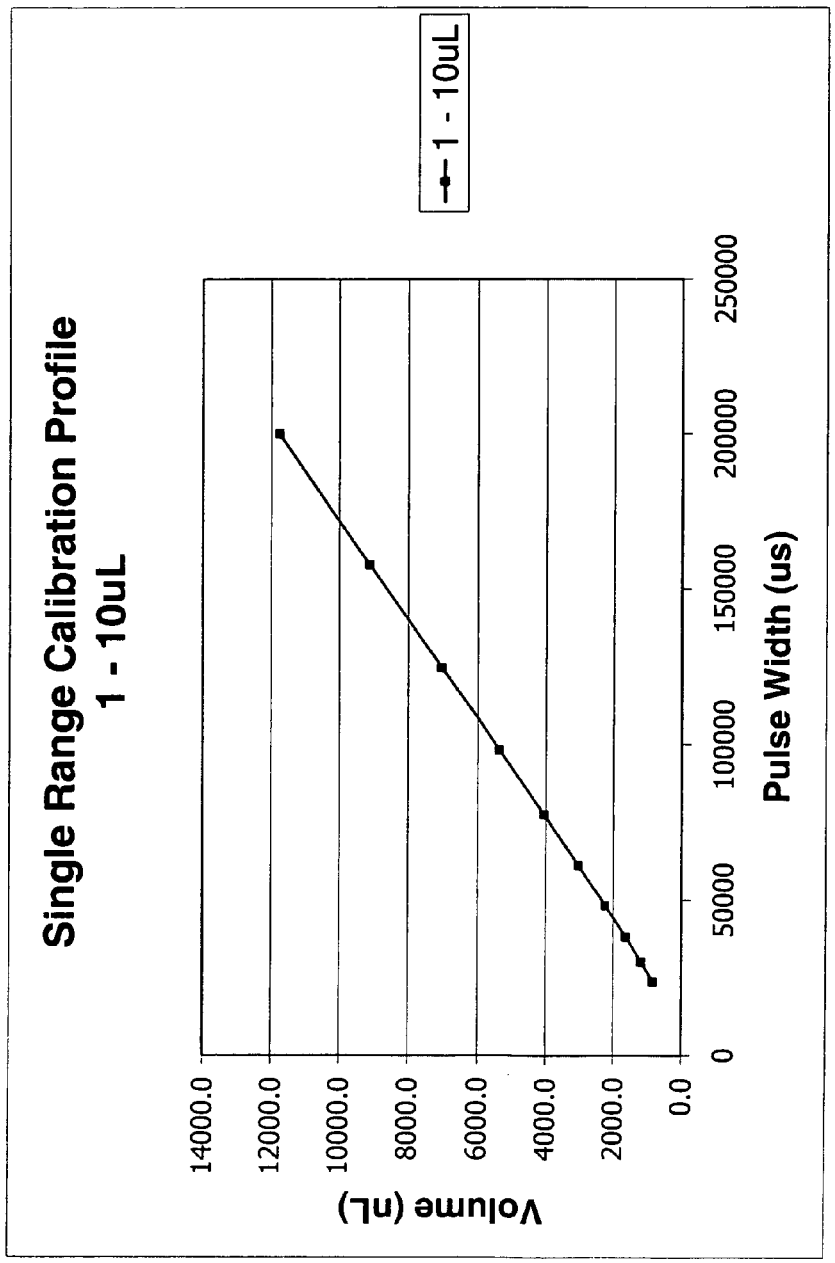
FIG. 14 is a graph of a Calibration Profile for dispense volumes ranging from 1.0 microliter to 10.0 microliters constructed in accordance with the calibration technique of the present invention.
Figure 15:
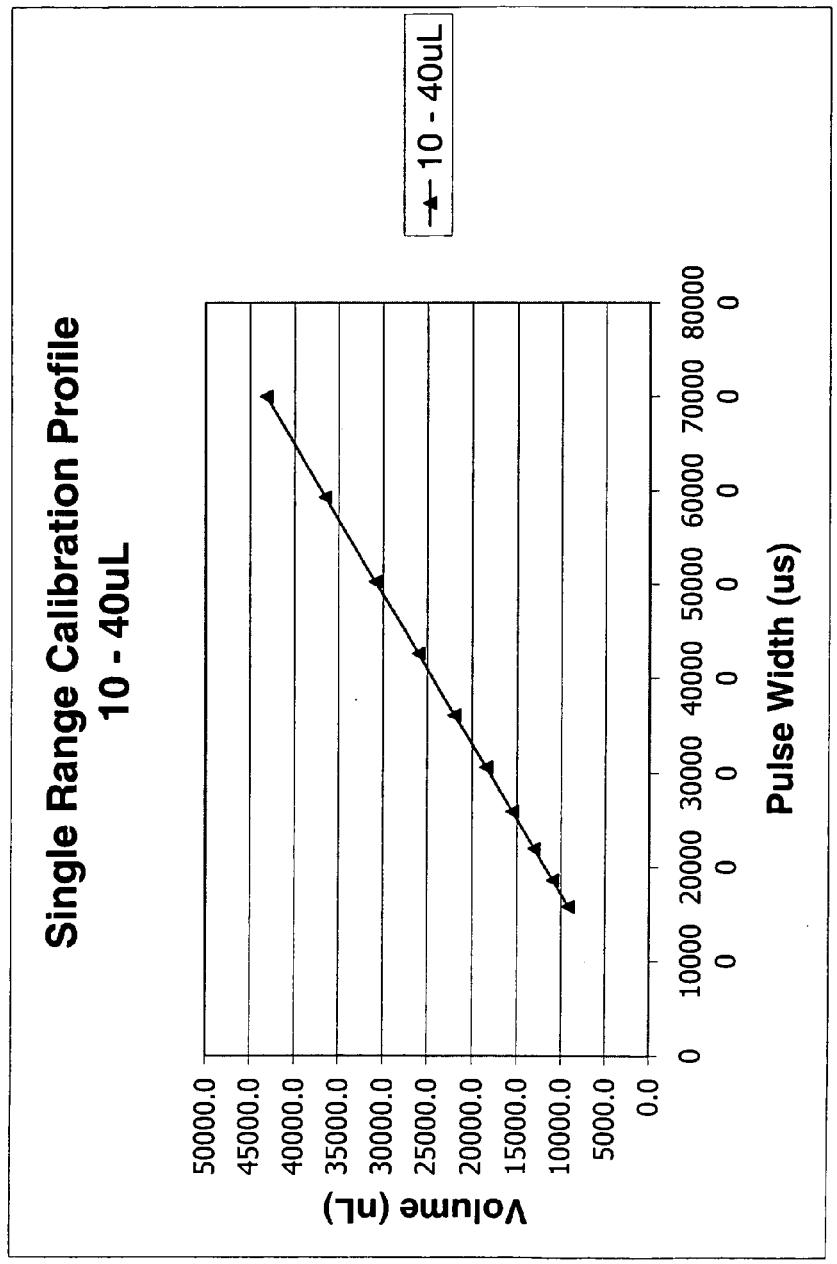
FIG. 15 is a graph of a Calibration Profile for dispense volumes ranging from 10.0 microliters to 40.0 microliters constructed in accordance with the calibration technique of the present invention.
Figure 16:
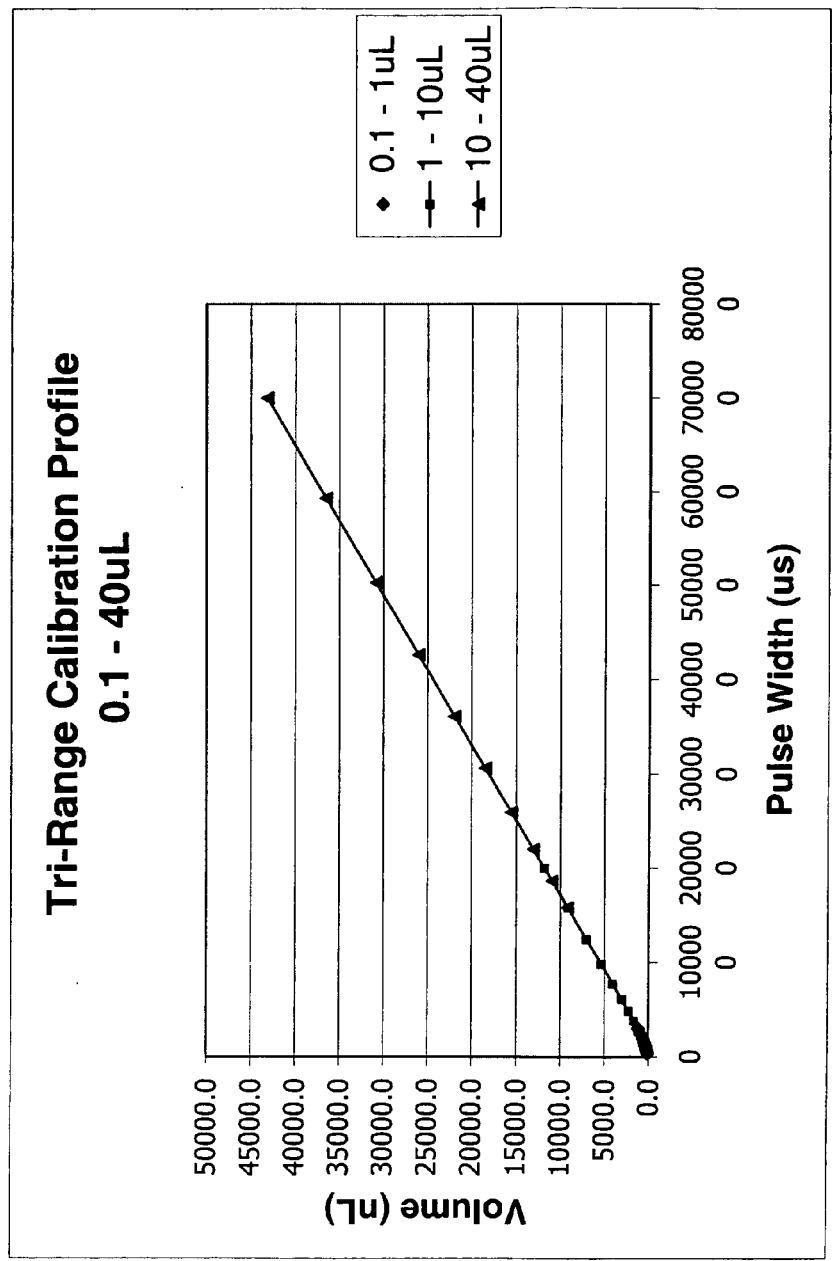
FIG. 16 is a graph of a Tri-Range Composite Calibration Profile for the Calibration Profiles of FIGS. 10, 14 and 15.
Figure 17:
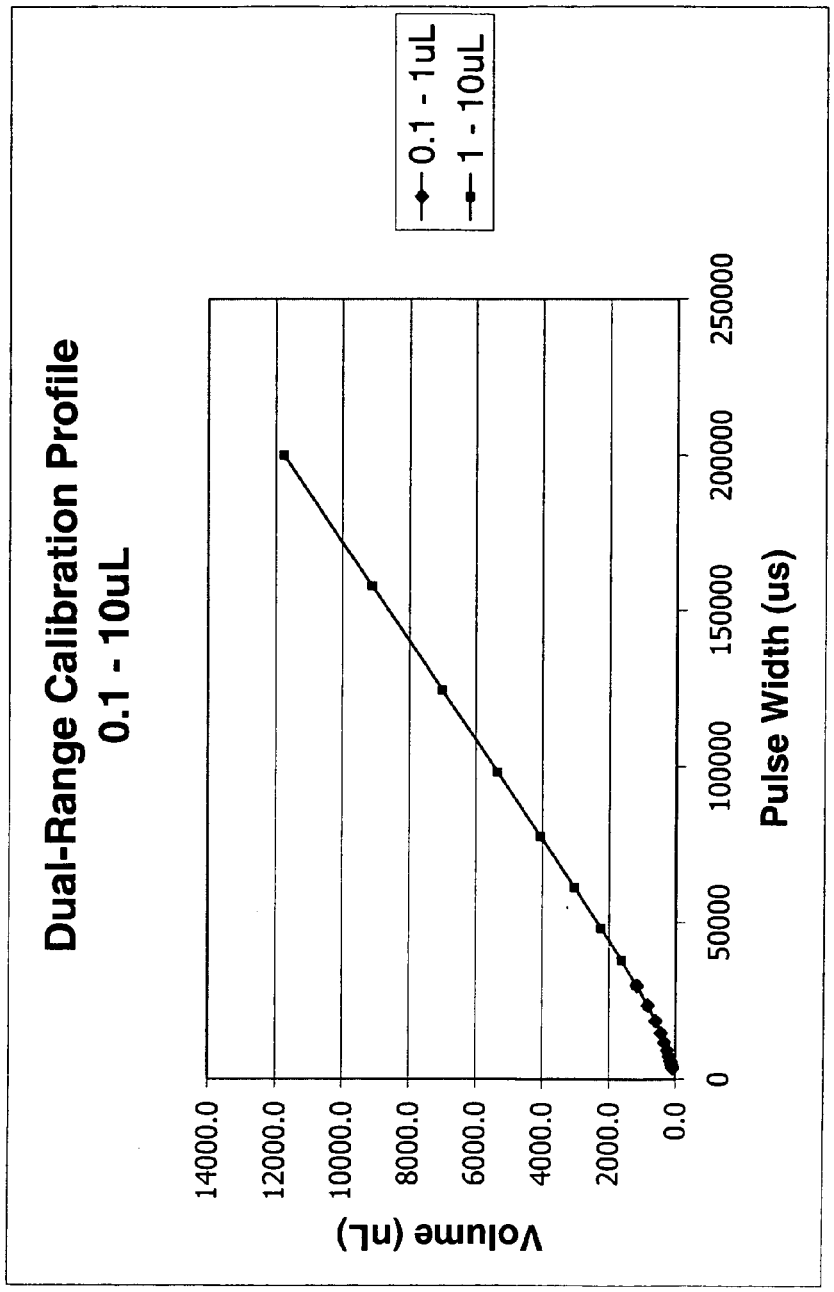
FIG. 17 is a graph of a Dual-Range Composite Calibration Profile for the Calibration Profiles of FIGS. 10 and 14.
Figure 18:
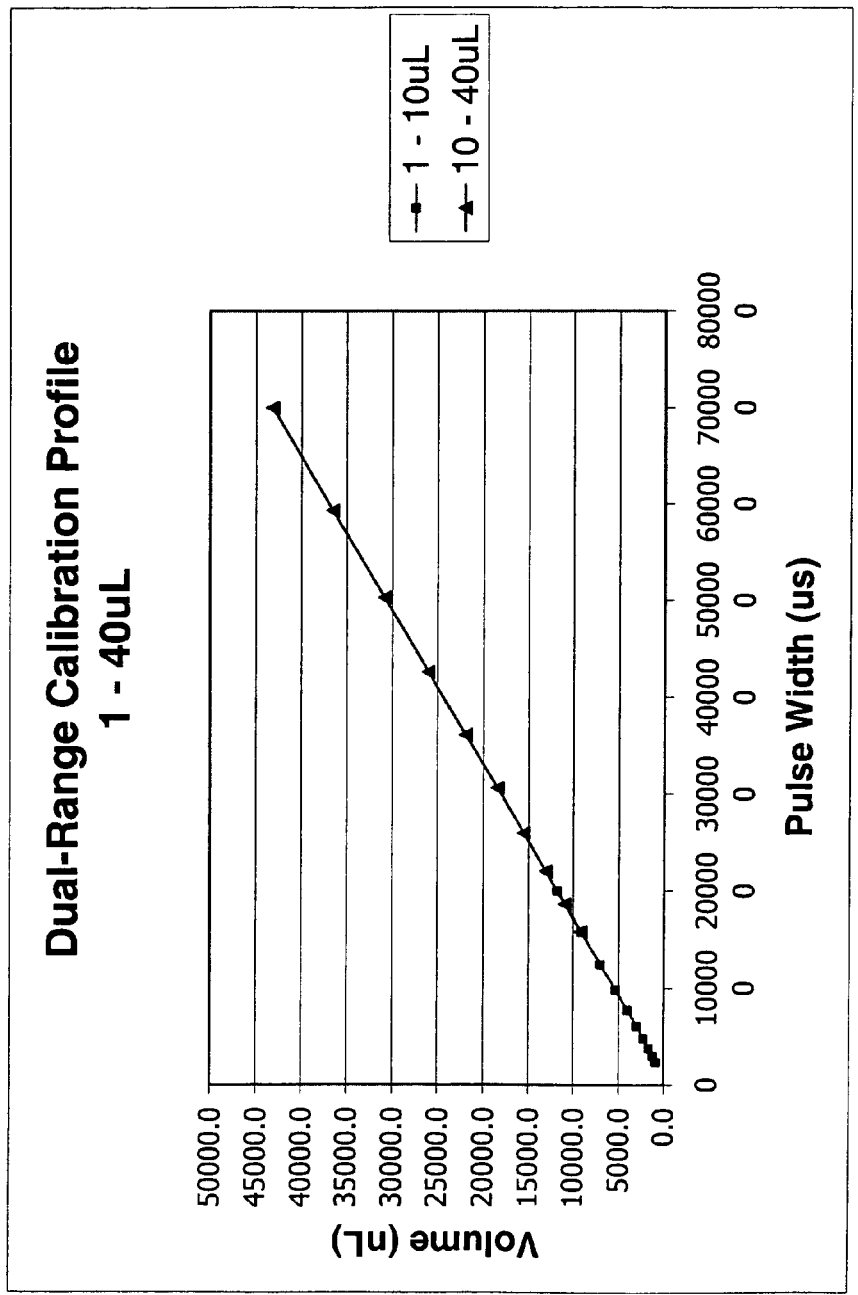
FIG. 18 is a graph of a Dual-Range Composite Calibration Profile for the Calibration Profiles of FIGS. 14 and 15.

Applying the above-mentioned calibration technique, the Calibration Profiles were constructed for each different volume range. For the first volume range in the range of 0.1 microliters to 1.0 microliter, the measured data of which is set forth in more detail in Table III of FIG. 13, the resulting Calibration Profile is shown in FIG. 10. Similarly, for the second volume range of 1.0 microliter to 10.0 microliters, the resulting Calibration Profile is shown in FIG. 14, while the third volume range of 10.0 microliters to 40.0 microliters yields the resulting Calibration Profile of FIG. 15. Depending upon the target volume dispensing range, these Calibration Profiles can be combined to yield a wider range Calibration Profile. FIGS. 16–18, accordingly, yield Tri-Range and Dual-Range Calibration Profiles, the data of which can be input into a software interface for automated operation. It will be appreciated that the interface need not be graphical. Further, while the profiles can be combined, the software and firmware can be adapted to support an number of data points (ten are exemplified in this example, and were provided to show that the calibration ranges overlap at 1 μL and 10 μL) in the final calibration table.

As previously mentioned, the initial pulse widths selected to prepare these Calibration Profiles are estimated using a lower base pulse width that will deliver a volume less that the lowest target volume for the calibrated range, and an uppermost ceiling pulse width that will deliver a volume that is greater than the highest target volume in the calibrated range. This is exemplified in the second volume range (i.e., 1.0 microliter to 10.0 microliters) of Table III of FIG. 13, where the lower base pulse width and associated dispense volume overlap the upper ceiling pulse width and associated dispense volume of the first volume range (i.e., 0.1 microliter to 1.0 microliter). Similarly, the upper ceiling pulse width and associated dispense volume of the second volume range overlap the lower base pulse width and associated dispense volume of the third volume range (i.e., 10.0 microliters to 40.0 microliters). In particular, in the second volume range of 1.0 microliter to 10.0 microliters, a lower base pulse width of 23,700 microseconds was selected which yielded a dispense volume of about 0.841 microliters. On the upper base end, a pulse width of 200,000 microseconds was selected which yielded a dispense volume of about 11.772 microliters.

In one technique to determine the intermediate pulses for the middle of this Calibration Profile, the lower base pulse width is divided into the upper ceiling pulse width to calculate the multiples of the base pulse width to the ceiling pulse width. The log of this quotient is then calculated to determine the multiplier that is used to calculate the pulse widths that will be used in the middle of the Calibration Profile.

As set forth below, and as exemplified in Table IV of FIG. 19, the data of which corresponds to that in Table III, the quotient of the second volume range is determined as follows:

200,000µs/23,700µs=8.438819.

Subsequently, Multiplier=Quotient$^{1/(number\ of\ calibration\ points)}$ Multiplier=1.267419.

A multiplier of 1.267419 is then calculated to determine the intermediary pulse widths. For example, 23,700 µs×1.267419=30,038 µs, while 30,038 µs×1.267419=38,071 µs, etc.

Using this curve-fitting technique of determining the pulse widths of the Calibration Profiles, calibrations can be developed for many ranges and numbers of calibration points. This curve-fitting technique is beneficial for several reasons. First, this technique provides the flexibility to calculate the pulse widths that are used within a calibration range, rather than guessing at pulse widths that will bracket the target dispense volume. Guessing leads to the necessity to perform iterations of each calibration until the correct one is determined. Secondly, the dispense volume relative to the pulse width appear to increase logarithmically. Therefore, selecting a lower base pulse width, and then a subsequent pulse width that is a logarithmic deviation from the base pulse width, rather than a linear deviation, should yield improved accuracy when the calibration profile is used in software to select the dispense pulse. Lastly, this technique spaces the subsequent pulse widths such that there are more points at the lower end of the curve and fewer points at the upper end of the curve (e.g., See the "Pulse Range" column in Table IV of FIG. 19). The time difference between point one and two is 956 µs, between point two and three 1210 µs, between points three and four 1532 µs, and the difference between all subsequent pulses are increasing to greater length of time.

Briefly, regarding the "Periods Pulse" column of Table IV of FIG. 19, the dispenser does not have the ability to dispense to the resolution of a single microsecond. The Xtal or Clock frequency is set to 20 microseconds. The instrument will receive a command to dispense at 3600 microseconds. The firmware will then convert this time to periods (3600 µs/(20 us/period))=180 periods. The dispense will then dispense for 180 periods of 20 microseconds. If the dispense time is not divisible by twenty or the set clock frequency the firmware will round the number of dispensing periods to the lower integer. A calculated pulse with of 4556 microseconds is converted to 227.8 periods with is the rounded to 228 periods or 4560 microseconds.

As mentioned above, the actual measurement of the dispensed volume from the dispensing orifices 35 can be determined using either a gravimetric calculation or spectrophotometric calculation. These two methods will be discussed briefly below.

With regard to the gravimetric calculation, this technique involves weighing of the dispensed fluid (i.e., gravimetric technique). By measuring the mass of fluid delivered after each pulse, the fluid volume delivered can be easily calculated and can be correlated to an open time of the respective solenoid valve. Typically, multiple pulses at a single pulse width are delivered to a container. The container and dispensed liquids are weighed to determine the weight of the dispensed liquid once the container weight is removed. The reason that multiple pulses are used in the calibration technique is to reduce any error in accuracy that would be caused by variances in precision from each individual dispense. Another technique, should the hardware configuration for each channel be substantially similar, is to simultaneously actuate each solenoid dispensing valve with identical pulse widths, and then average the measured dispensing volumes for each channel. In this manner, a systematic, as opposed to individual, calibration may be performed.

The volume of fluid delivered with each pulse is determined by the following equation:

Volume(nL)=Density(g/mL)/(total mass(g)−tare mass (g))*(1×10$^6$ nL/mL)/(Number of Pulses)* (Number of Tips).

As mentioned The pulse widths used to prepare these Calibration Profiles are calculated by starting with a lower base pulse width that will deliver a volume less that the lowest target volume for the calibrated range and an uppermost ceiling pulse width that will deliver a volume that is greater than the highest target volume in the calibrated range. The lower base pulse is then divided into the upper ceiling pulse to calculate the multiples of the base pulse to the ceiling pulse. The log of this quotient is then calculated to determine the pulses that will be used in the middle of the Calibration Profile. Using this technique of determining the pulses of the Calibration Profiles, calibrations can be developed for many ranges and numbers of calibration points. Different pulse widths are used for each calibration point such that the total masses of all of the final volumes are similar. In this manner the scale is always measuring a similar mass. However, in order to maintain a statistically significant number of pulses for calibration, each calibration point preferably applies a minimum of ten pulses.

Regarding the spectrophotometric volume calculation (or fluorescent calibration method), a technique is used where liquid dispensing occurs at several different pulse widths (i.e., valve open time periods) into a microplate capable of optimal fluorescence. The plate used in this method is usually black plate, due to the low background. By measuring the fluorescence within each well and comparing that fluorescence to a standard curve, a volume can be calculated. Once the volume is known then the relationship of volume and pulse width can be plotted on an graph. Multiple pulses at a single pulse are delivered to single well of a microtiter plate and the total fluorescence is measured in a fluorescent plate reader. The reason that multiple pulse widths are used in the calibration technique is to reduce any error in accuracy that would be caused by variances in precision from each individual dispense. The tables in the gravimetric section below show pulses used to calibrate the dispenser in three different volume ranges 100 to 1,000 nL, 1,000 to 10,000 nL and 10,000 to 40,000 nL.

The sequence of events to calibrate with the fluorescent method are outlined below:

Dispense in to a black microplate

Add diluent to the microplate

Shake the plate for one minute

Read the plate

Calculate volume from the fluorescent standard curve, calculations below.

Volume delivery calculation

Export calibration plate and dispense plate RFU (relative fluorescence units) data to Excel Calculate linear regression slope for the calibration plate Convert RFU data on the dispense plate to concentration Calculate the volume of dye delivered to each well Concentration Dye Dispensed $y = Mx + b$ (slope of the linear regression)

Volume calculation—Two Methods $V_1 = (C_2 V_2)/C_1$ use if $V_2 \gg V_1$ $C_2$ = value obtained from linear regression
$C_1$ = Stock solution concentration (~500,000 nmol/L)
$V_2$ = volume of diluent added
100 uL = 100,000 nL
500 nL added to 100 uL ~ Error of 0.5%

$C_1 V_1 = C_2 V_2$ use if $V_2 \sim V_1$ $C_1 V_1 = C_2 (V_1 + V_{dil})$ $C_1 V_1 = C_2 V_1 + C_2 V_{dil}$ $C_1 V_1 - C_2 V_1 = C_2 V_{dil}$ $V_1 (C_1 - C_2) = C_2 V_{dil}$ $V_1 = (C_2 V_{dil})/(C_1 - C_2)$ $C_2$ = value obtained from linear regression
$C_1$ = Stock solution concentration (~500,000 nmol/L)
$V_{dil}$ = volume of diluent delivered to the well Again, the pulse widths used to prepare these Calibration Profiles are calculated by starting with a lower base pulse width that will deliver a volume less that the lowest target volume for the calibrated range and an uppermost ceiling pulse width that will deliver a volume that is greater than the highest target volume in the calibrated range. The lower base pulse width is then divided into the upper ceiling pulse width to calculate the multiples of the base pulse to the ceiling pulse. The log of this quotient is then calculated to determine the pulses that will be used in the middle of the Calibration Profile. Different pulses are used for each calibration point such that the total masses of all of the final volumes are similar. In this manner the scale is always measuring a similar mass. This is even more important when the calibration transitions to a fluorescent method for calibration. Fluorescent microplate readers have linear ranges that are much narrower than analytical scales. However, in order to maintain a statistically significant number of pulses for calibration, each calibration point preferably applies a minimum of ten pulses.

Although only a few embodiments of the present inventions have been described in detail, it should be understood that the present inventions may be embodied in many other specific forms without departing from the spirit or scope of the inventions.

What is claimed is:

1. A method of purging trapped gas from a system fluid contained in one or more interior areas of an actuation valve that selectively fluidly inter-couples a fluid communication line to a pressurized system fluid reservoir providing the system fluid, said fluid communication line defining a communication passageway extending from a dispensing orifice thereof to the actuation valve, said method comprising:

pressurizing the system fluid in the system fluid reservoir with a pressurized gas;

priming the actuation valve and the fluid communication line by initially flowing the system fluid, via said pressurized gas, through the actuation valve and into said communication passageway for dispensing through the dispensing orifice such that said actuation valve and said communication passageway are converted from a generally dry state to a hydraulic state; and rapidly actuating the actuation valve between a closed condition, preventing flow of said system fluid through said actuation valve from said system fluid reservoir to the dispensing orifice, and an opened condition, enabling fluid flow and dispensing of the system fluid through said dispensing orifice, at at least two different discrete actuation frequencies each for a respective predetermined period of time in a manner purging and expelling trapped gases contained in the areas of said actuation valve.

2. The method according to claim 1, wherein
said pressurizing the system fluid includes providing a substantially constant gas pressure to maintain a substantially constant pressure head at the actuation valve.

3. The method according to claim 1, wherein
said rapidly actuating the actuation valve at the respective discrete frequencies for said respective predetermined periods of time is performed a set number of times.

4. The method according to claim 2, wherein
said rapidly actuating the actuation valve is performed by varying the actuation frequency at a plurality of set discrete frequencies, each actuation at one of the discrete frequencies being for a respective predetermined period of time.

5. The method according to claim 2, wherein
said plurality of discrete frequencies are in the range of about 1 Hz to about 1750 Hz.

6. The method according to claim 5 wherein
said plurality of discrete frequencies are in the range of about 10 Hz to about 420 Hz.

7. The method according to claim 4, further including:
actuating the actuation valve at each discrete frequency for said respective predetermined period of time a respective set number of times.

8. The method according to claim 4, wherein
said varying the actuation frequency is performed by a ramped frequency sweep, incrementally increasing the actuation frequency at said discrete frequencies.

9. The method according to claim 8, wherein
said incrementally increasing the actuation frequency is performed in the range from about 10 Hz to about 420 Hz.

10. The method according to claim 4, wherein
said varying the actuation frequency is performed by a ramped frequency sweep, incrementally decreasing the actuation frequency at said discrete frequencies.

11. The method according to claim 2, wherein
said gas pressure is in the range of about 2.0 psi to about 15.0 psi.

12. The method according to claim 11, wherein
said gas pressure is about 8.0 psi.

13. The method according to claim 11, wherein
said pressurizing the system fluid includes selecting a pressurizing gas that suppresses in-gassing, and is substantially insoluble to the system fluid.

14. The method according to claim 13, wherein
said pressurizing gas is helium.

15. A method of simultaneous purging trapped gas from system fluid contained in respective interior areas of a plurality of respective actuation valves, each selectively fluidly inter-couples a respective fluid communication line to a pressurized system fluid reservoir providing the system fluid, each respective fluid communication line defines a respective communication passageway extending from a respective dispensing orifice thereof to the respective actuation valve, said method comprising:

(a) pressurizing the system fluid of the system fluid reservoir with a pressurized gas;
(b) priming each actuation valve and respective communication line by simultaneously flowing the system fluid, via said pressurized gas, through each actuation valve and into each respective communication passageway for dispensing through each respective dispensing orifice thereof such that each actuation valve and each said communication passageway is converted from a generally dry state to a hydraulic state; and
(c) simultaneously rapidly actuating each actuation valve between a respective closed condition, preventing flow of said system fluid therethrough from said system fluid reservoir to the respective dispensing orifice thereof, and a respective opened condition, enabling fluid flow and dispensing of the system fluid through each respective dispensing orifice, at a discrete actuation frequency for a respective predetermined period of time such that trapped gases contained in the interior areas of each respective actuation valve are purged and expelled therefrom.

16. The method according to claim 15, wherein
said pressurizing the system fluid includes providing a substantially constant gas pressure to said system fluid reservoir to maintain a substantially constant pressure head at each actuation valve.

17. The method according to claim 15, wherein
said simultaneously rapidly actuating each actuation valve for said respective predetermined period of time are each performed a set number of times.

18. The method according to claim 15, wherein
said simultaneously rapidly actuating each actuation valve is performed by varying the actuation frequency at a plurality of set discrete frequencies, each actuation at one of the discrete frequencies being for a respective predetermined period of time.

19. The method according to claim 18 wherein
said plurality of discrete frequencies are in the range of about 10 Hz to about 420 Hz.

20. The method according to claim 18, further including:
actuating each actuation valve at each discrete frequency for said respective predetermined period of time a respective set number of times.

21. The method according to claim 20, wherein
said varying the actuation frequency is performed by a ramped frequency sweep, incrementally increasing the actuation frequency at said discrete frequencies.

22. The method according to claim 21, wherein
said incrementally increasing the actuation frequency is performed in the range from about 10 Hz to about 420 Hz.

23. The method according to claim 18, wherein
said varying the actuation frequency is performed by a ramped frequency sweep, incrementally decreasing the actuation frequency at said discrete frequencies.

24. The method according to claim 16, wherein
said pressurizing the system fluid is performed by supplying the pressurizing gas in the range of about 2.0 psi to about 15.0 psi.

25. The method according to claim 24, wherein
said pressurizing the system fluid is performed by supplying the pressurizing gas in the range of about 8.0 psi.

26. The method according to claim 24, further including:
selecting a pressurizing gas that suppresses in-gassing, and is substantially insoluble to the system fluid.

27. The method according to claim 26, wherein
said selecting a pressurizing gas includes selecting helium.

28. The method according to claim 15, further including:
(c) actuating each said actuation valve from the closed condition to the opened condition and back to the closed condition for substantially the same time period to respectively dispense system fluid from each dispensing orifice of the respective communication line;
(d) measuring the volume of system fluid dispensed from each dispensing orifice;
(e) calculating the mean variance of the measured volumes;
(f) for each communication line having a measured volume of system fluid varying from the mean variance by more than a predetermined percentage, repeating event (b).

29. The method according to claim 28, further including:
repeating events (c)–(f) until the respective dispense volume for each communication line does not vary from the mean variance by more than the predetermined percentage.

30. The method according to claim 28, wherein
said predetermined percentage is in the range of about 3% to about 7%.

31. The method according to claim 30, wherein
said predetermined percentage is in the range of about 5%.

32. The method according to claim 1, further including:
after rapidly actuating the actuation valve, purging the actuation valve and the communication line of the expelled and purged trapped gases by flowing the system fluid, via said pressurized gas, through the actuation valve and out the dispensing orifice of the communication line.

33. The method according to claim 15, further including:
after simultaneously rapidly actuating each actuation valve, simultaneously purging each respective actuation valve and the corresponding communication line of the expelled and purged trapped gases by simultaneously flowing the system fluid, via said pressurized gas, through each respective actuation valve and out the corresponding dispensing orifice of the respective communication line.

34. A method of purging trapped gas from a system fluid contained in one or more interior areas of an actuation valve that selectively fluidly inter-couples a fluid communication line to a pressurized system fluid reservoir providing the system fluid, said fluid communication line defining a communication passageway extending from a dispensing orifice thereof to the actuation valve, said method comprising:

pressurizing the system fluid in the system fluid reservoir with a pressurized gas;
priming the actuation valve and the fluid communication line by initially flowing the system fluid, via said pressurized gas, through the actuation valve and into the communication passageway for dispensing through the dispensing orifice such that said actuation valve and said communication passageway are converted from a generally dry state to a hydraulic state;
rapidly actuating the actuation valve between a closed condition and an opened condition at a discrete actuation frequency for a predetermined period of time such that the trapped gases contained in the areas of said actuation valve are purged and expelled therefrom; and after rapidly actuating the actuation valve, purging the actuation valve and the communication line of the expelled and purged trapped gases by flowing the system fluid, via said pressurized gas, through the actuation valve, the communication passageway and out the dispensing orifice of the communication line.

35. The method according to claim 34, wherein said pressurizing the system fluid includes providing a substantially constant gas pressure to maintain a substantially constant pressure head at the actuation valve.

36. The method according to claim 35, wherein said rapidly actuating the actuation valve is performed by varying the actuation frequency at a plurality of set discrete frequencies, each actuation at one of the discrete frequencies being for a respective predetermined period of time.

37. The method according to claim 36, wherein said plurality of set discrete frequencies are in the range of about 1 Hz to about 1750 Hz.

38. The method according to claim 36, wherein said varying the actuation frequency is performed by a ramped frequency sweep, incrementally increasing the actuation frequency at said discrete frequencies.

39. The method according to claim 38, wherein said incrementally increasing the actuation frequency is performed in the range from about 10 Hz to about 420 Hz.

40. The method according to claim 36, wherein said varying the actuation frequency is performed by a ramped frequency sweep, incrementally decreasing the actuation frequency at said discrete frequencies.

41. The method according to claim 34, wherein said gas pressure is in the range of about 2.0 psi to about 15.0 psi.

42. The method according to claim 34, wherein said pressurizing the system fluid includes selecting a pressurizing gas that suppresses in-gassing, and is substantially insoluble to the system fluid.

* * * * *